United States Patent
Tai

(10) Patent No.: US 11,865,346 B2
(45) Date of Patent: Jan. 9, 2024

(54) NERVE BLOCK BY ELECTRICAL PULSES AT SUB-THRESHOLD INTENSITY

(71) Applicant: University of Pittsburgh—Of the Commonwealth System of Higher Education, Pittsburgh, PA (US)

(72) Inventor: Changfeng Tai, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 104 days.

(21) Appl. No.: 17/047,754

(22) PCT Filed: Apr. 15, 2019

(86) PCT No.: PCT/US2019/027471
§ 371 (c)(1),
(2) Date: Oct. 15, 2020

(87) PCT Pub. No.: WO2019/204198
PCT Pub. Date: Oct. 24, 2019

(65) Prior Publication Data
US 2021/0106831 A1    Apr. 15, 2021

Related U.S. Application Data

(60) Provisional application No. 62/658,147, filed on Apr. 16, 2018.

(51) Int. Cl.
*A61N 1/36* (2006.01)
*A61N 1/05* (2006.01)

(52) U.S. Cl.
CPC ....... *A61N 1/36164* (2013.01); *A61N 1/0551* (2013.01); *A61N 1/36062* (2017.08);
(Continued)

(58) Field of Classification Search
CPC .............. A61N 1/36164; A61N 1/0551; A61N 1/36062; A61N 1/36071; A61N 1/36153;
(Continued)

(56) References Cited

U.S. PATENT DOCUMENTS

2004/0127953 A1* 7/2004 Kilgore .............. A61N 1/36164
607/46
2006/0190053 A1   8/2006 Dobak
(Continued)

FOREIGN PATENT DOCUMENTS

JP        2011502586 A        1/2011

OTHER PUBLICATIONS

Peng, et. al, "Influence of stimulus waveforms of high-frequency electrical current on nerve conduction block," 2009 4th International IEEE/EMBS Conference on Neural Engineering, 2009, pp. 72-75, doi: 10.1109/NER.2009.5109237 (Year: 2009).*
(Continued)

*Primary Examiner* — Carl H Layno
*Assistant Examiner* — Anh-Khoa N Dinh
(74) *Attorney, Agent, or Firm* — The Webb Law Firm

(57) ABSTRACT

Provided herein is a method of blocking a nerve or neuron by applying an electrical stimulation to the nerve or neuron, wherein the electrical stimulation is of an intensity below the excitation threshold of the nerve or neuron for a length of time sufficient to produce a block of nerve conduction or neuron excitation.

19 Claims, 12 Drawing Sheets

(52) U.S. Cl.
CPC ..... *A61N 1/36071* (2013.01); *A61N 1/36153* (2013.01); *A61N 1/36157* (2013.01)

(58) Field of Classification Search
CPC ............ A61N 1/36157; A61N 1/36167; A61N 1/36171; A61N 1/3606; A61N 1/36007; A61N 1/0553; A61N 1/0558; A61N 1/36057; A61N 1/36064; A61N 1/36067; A61N 1/36107; A61N 1/36125; A61N 1/36175; A61N 1/362; A61N 1/37229; A61N 1/37235; A61N 1/37247; A61N 1/37252; A61N 1/37288; A61N 1/3787; A61N 2/002; A61N 2/006; A61N 2/008
See application file for complete search history.

(56) References Cited

U.S. PATENT DOCUMENTS

| | | | |
|---|---|---|---|
| 2007/0027486 | A1* | 2/2007 | Armstrong ......... A61N 1/36071 607/45 |
| 2007/0173908 | A1* | 7/2007 | Begnaud ............ A61N 1/36082 607/2 |
| 2008/0065158 | A1 | 3/2008 | Ben-Ezra et al. |
| 2009/0036945 | A1 | 2/2009 | Chancellor et al. |
| 2009/0204173 | A1 | 8/2009 | Fang et al. |
| 2010/0036454 | A1 | 2/2010 | Bennett et al. |
| 2013/0035740 | A1* | 2/2013 | Sharma .............. A61N 1/36171 607/40 |
| 2013/0158627 | A1 | 6/2013 | Gozani et al. |
| 2013/0238049 | A1 | 9/2013 | Simon et al. |
| 2015/0032181 | A1 | 1/2015 | Baynham et al. |
| 2015/0265836 | A1 | 9/2015 | Simon et al. |
| 2017/0095667 | A1 | 4/2017 | Yakovlev et al. |
| 2017/0348540 | A1 | 12/2017 | Doan et al. |
| 2018/0085580 | A1 | 3/2018 | Perez et al. |

OTHER PUBLICATIONS

Apovian et al., "Two-Year Outcomes of Vagal Nerve Blocking (vBloc) for the Treatment of Obesity in the ReCharge Trial", Obes Surg, 2017, pp. 169-176, vol. 27.
Bhadra et al., "High-Frequency Electrical Conduction Block of Mammalian Peripheral Motor Nerve", Muscle Nerve, 2005, pp. 782-790, vol. 32.
Bhadra et al., "Temporary persistence of conduction block after prolonged Filohertz Frequency Alternating Current (KHFAC) on rat sciatic nerve", J Neural Eng, 2018, pp. 1-15, vol. 15:1.
Cattell et al., "The "Inhibitory" Effect of High-Frequency Stimulation and the Excitation State of Nerve.", J Physiol, 1934, pp. 407-415.
Clausen, "Quantification of Na+,K+ pumps and their transport rate in skeletal muscle: Functional significance", J Gen Physiol, 2013, pp. 327-345, vol. 142:4.
Cuellar et al., "Effect of High-Frequency Alternating Current on Spinal Afferent Nociceptive Transmission", Neuromodulation, 2013, pp. 318-327, vol. 16.
Finch et al., "High-Frequency (10 KHz) Electrical Stimulation of Peripheral Nerves for Treating Chronic Pain: A Double-Blind Trial of Presence vs Absence of Stimulation", Neuromodulation, 2019, pp. 529-536, vol. 22.
Floras, "Sympathetic Nervous System Activation in Human Heart Failure", J Am Coll Cardiol, 2009, pp. 375-385, vol. 54:5.
Franz et al. "Mechanisms for Differential Block Among Single Myelinated and Non-Myelinated Axons by Procaine", J Physiol, 1974, pp. 193-210, vol. 236.
Fudim et al., "Splanchnic Nerve Block for Acute Heart Failure", Circulation, 2018, pp. 951-953, vol. 138:9.
Gaunt et al., "Transcutaneously Coupled, High-Frequency Electrical Stimulation of the Pudendal Nerve Blocks External Urethral Sphincter Contractions", Neurorehabil Neural Repair, 2009, pp. 615-626, vol. 23:6.
Hoogeveen et al., "Ultrastructural changes in the rat sciatic nerve after local hyperthermia", Int J Hyperthermia, 1993, pp. 723-730, vol. 9:5.
Jia et al., "Cold Nerve Injury is Enhanced by Intermittent Cooling", Muscle & Nerve, 1999, pp. 1644-1652, vol. 22.
Klumpp et al., "Irreversible Differential Block of A- and C-Fibres Following Local Nerve Heating in the Cat", J Physiol, 1980, pp. 471-482, vol. 298.
Liu et al., "Post stimulus effects of high frequency biphasic electrical current on a fibre's conductibility in isolated frog nerves", J Neural Eng, 2013, pp. 1-14, vol. 10.
Liu et al., "Use Dependence of Heat Sensitivity of Vanilloid Receptor TRPV2", Biophysical J, 2016, pp. 1523-1537, vol. 110.
Miles et al., "Effects of ramped amplitude waveforms on the onset response of high-frequency mammalian nerve block", J. Neural Eng., 2007, pp. 390-398, vol. 4.
Paintal, "Block of Conduction in Mammalian Myelinated Nerve Fibres by Low Temperatures", J Physiol, 1965, pp. 1-19, vol. 180.
Pertusa et al., "Mutagenesis and Temperature-Sensitive Little Machines", Mutagenesis, InTech Open Access, 2012, pp. 221-246.
Reboul et al., "The Action of Alternating Currents Upon the Electrical Excitability of Nerve", The American Journal of Physiology, 1939, pp. 205-215, vol. 125:2.
Rosenblueth et al., "The Blocking and Deblocking Effects of Alternating Currents on Nerve", Am J Physiol, 1939, pp. 251-264.
Sarr et al., "The EMPOWER Study: Randomized, Prospective, Double-Blind, Multicenter Trial of Vagal Blockade to Induce Weight Loss in Morbid Obesity", Obes Surg, 2012, pp. 1771-1782.
Soin et al., "High-Frequency Electrical Nerve Block for Postamputation Pain: A Pilot Study", Neuromodulation, 2015, pp. 197-206, vol. 18.
Stecker et al., "Peripheral nerve at extreme low temperatures 1: Effects of temperature on the action potential", Crybioloy, 2009, pp. 1-11, vol. 59.
Tai et al., "Block of External Urethral Sphincter Contraction by High Frequency Electrical Stimulation of Pudendal Nerve", The Journal of Urology, 2004, pp. 2069-2072, vol. 172.
Tai et al., "Simulation of Nerve Block by High-Frequency Sinusoidal Electrical Current Based on the Hodgkin-Huxley Model", IEEE Transactions on Neural Systems and Rehabilitation Engineering, 2005, pp. 415-422, vol. 13:3.
Vujaskovic et al., "Effects of intraoperative hyperthermia on peripheral nerves: Neurological and electrophysiological studies", Int J Hyperthermia, 1994, pp. 41-49, vol. 10:1.
Waataja et al., "Effects of high-frequency alternating current on axonal conduction through the vagus nerve", J Neural Eng, 2011, pp. 1-8, vol. 8.
Yang et al., "Pudendal Nerve Stimulation and Block by a Wireless Controlled Implantable Stimulator in Cats", Neuromodulation, 2014, pp. 490-496, vol. 17:5.
Yang et al., "Post-Stimulation Block of Frog Sciatic Nerve by High-Frequency (kHz) Biphasic Stimulation", Med Biol Eng Comput, 2017, pp. 585-593, vol. 55:4.
Zhang et al., "Mechanism of Nerve Conduction Block Induced by High-Frequency Biphasic Electrical Currents", IEEE Trans Biomed Eng., 2006, pp. 2445-2454, vol. 53.
Zhang et al., "Conduction block of mammalian myelinated nerve by local cooling to 15-30° C. after a brief heating", J Neurophysiol, 2016, pp. 1436-1445, vol. 115:3.
Liu et al., "The Role of Slow Potassium Current in Nerve Conduction Block Induced by High-Frequency Biphasic Electrical Current," IEE Transactions on Biomedical Engineering, Jan. 2009, pp. 137-146, vol. 56, No. 1.
Liu et al., "Post stimulus effects of high frequency biphasic electrical current on a fibre's conductibility in isolated frog nerves," J. Neural Eng., 2013, 13 pages, vol. 10.

* cited by examiner

NERVE BLOCK BY ELECTRICAL PULSES AT SUB-THRESHOLD INTENSITY

CROSS-REFERENCE TO RELATED APPLICATIONS

This application is the United States national phase of International Application No. PCT/US2019/027471 filed Apr. 15, 2019, and claims priority to U.S. Provisional Patent Application No. 62/658,147, filed Apr. 16, 2018, the disclosures of which are hereby incorporated by reference in their entirety.

STATEMENT REGARDING FEDERALLY SPONSORED RESEARCH

This invention was made with government support under Grant No. DK068566 awarded by the National Institutes of Health. The government has certain rights in the invention.

BACKGROUND

Field of the Invention

Provided herein is a method of nerve block and related devices, more specifically a method of blocking nerve conduction or neuron excitation by applying sub-threshold electrical pulses to the nerve or neuron, and devices for carrying out such methods.

Description of Related Art

Blocking nerve conduction or neuron excitation has a broad clinical application to treat many disorders including chronic pain, obesity, heart failure, bladder dysfunction or spasm after spinal cord injury, etc. However, currently electrical nerve block uses kilohertz electrical pulses in clinical applications, which always produce initial nerve excitation because the kilohertz pulses must have a stimulation intensity above the minimal intensity for inducing nerve excitation, that is, they have a super-threshold intensity. The initial excitation is problematic, for example, it generates initial strong pain and potential for physical damage due to dangerous muscle contractions before it can block the pain. It also produces paresthesia sensation (vibration, pressure, numbness, etc.) that is not tolerable for many patients.

Accordingly, there is a need in the art for a method of blocking nerve conduction to provide relief or otherwise treat a condition, while avoiding the shortcomings that accompany use of super-threshold intensity currently necessary to provide such blocking.

SUMMARY

In view of the above need, disclosed herein is a new method to block a nerve/neuron by electrical pulses using a sub-threshold intensity, e.g., the intensity is below the minimal intensity required to excite the nerve/neuron. By blocking a nerve/neuron, signals transmitted along such nerves or through the neurons, such as pain signals, can be blocked, thus treating, by reducing or eliminating, pain.

Accordingly, provided herein is a method of blocking a nerve or neuron by applying an electrical stimulation to the nerve or neuron, wherein the electrical stimulation is of an intensity that does not cause the nerve or neuron excitation for a length of time sufficient to produce a block of nerve conduction or neuron excitation.

Also provided herein is a device including a controller; a pulse generator in communication with the controller; and an electrode in electrical communication with the pulse generator, wherein the device is configured to apply an electrical stimulation to the nerve/neuron, wherein the electrical stimulation is of an intensity configured to increase an initial excitation threshold of the nerve/neuron for a length of time sufficient to produce a block of nerve conduction or neuron excitation.

Also provided herein is a device including a controller; a pulse generator in communication with the controller; and one or more skin surface electrodes or magnetic coils in electrical communication with the pulse generator, wherein the pulse generator and one or more skin surface electrodes or magnetic coils are configured to apply an electrical stimulation to a nerve or neuron, wherein the electrical stimulation is of an intensity below an initial excitation threshold of the nerve or neuron for a length of time sufficient to produce a block of nerve conduction or neuron excitation.

Also provided herein is a method of reducing peripheral pain in a patient by applying an electrical stimulation to a peripheral nerve or a group of central neurons, wherein the electrical stimulation is of an intensity that does not cause nerve or neuron excitation for a length of time sufficient to produce a block of nerve conduction or neuron excitation, thereby reducing peripheral pain.

Further embodiments or aspects are provided in the below clauses:

Clause 1: A method of blocking a nerve or neuron in a patient, comprising applying sub-threshold electrical pulses to the nerve or neuron (that is, by applying the electrical pulses on or near the nerve or neuron) for a length of time able to produce a block of the nerve/neuron.

Clause 2: The method of clause 1, wherein the electrical pulses are biphasic.

Clause 3: The method of clause 2, wherein the biphasic pulses are symmetric between the positive and negative phases of the biphasic pulse.

Clause 4: The method of clause 2, wherein the biphasic pulses are asymmetric between the positive and negative phases of the biphasic pulse.

Clause 5: The method of clause 1, wherein the electrical pulses are charge-balanced.

Clause 6: The method of any of clauses 1-5, wherein the electrical pulses have a frequency high enough to change intracellular and extracellular ion concentrations to block nerve conduction or block neuron excitation after applying the pulses for a period of time.

Clause 7: The method of any of clauses 1-6, wherein the frequency of the electrical pulses is faster than the speed for the sodium-potassium pump of the nerve or neuron to recover the intracellular and extracellular ion concentrations that are changed by the electrical pulses.

Clause 8: The method of any of clauses 1-7, wherein the frequency of the electrical pulses is greater than 1 Hz for blocking a nerve.

Clause 9: The method of any of clauses 1-7, wherein the frequency of the electrical pulses is in the range of from 1 Hz to 50 kHz.

Clause 10: The method of any of clauses 1-7, wherein the frequency of the electrical pulses is greater than 1 Hz for blocking a neuron.

Clause 11: The method of clause 10, wherein the frequency of the electrical pulses is in the range of from 1 Hz to 50 kHz.

Clause 12: The method of any of clauses 1-6, wherein the sub-threshold electrical pulses are applied for a time period of at least 1 minute.

Clause 13: The method of clause 12, wherein the sub-threshold electrical pulses are applied for a time period in the range of from 5 minutes to 300 minutes.

Clause 14: The method of clause 12, wherein the sub-threshold electrical pulses are applied for a time period in the range of from 5 hours to 5 days.

Clause 15: The method of any of clauses 1-14, wherein the sub-threshold pulses are applied at an intensity below an initial excitation threshold of the nerve or neuron for a suitable time period sufficient to cause an increase of the excitation threshold of the nerve or neuron to a first increased excitation threshold, and the intensity of the sub-threshold electrical pulses is then raised above the initial excitation threshold of the nerve or neuron and below the first increased excitation threshold of the nerve or neuron and applied for a length of time to further raise the first increased excitation threshold to a second increased excitation threshold.

Clause 16: The method of clause 15, further comprising, after raising the first increased excitation threshold to a second increased excitation threshold, raising the intensity of the sub-threshold electrical pulses above the first increased excitation threshold of the nerve or neuron and below the second increased excitation threshold of the nerve or neuron and applied for a length of time to further raise the second increased excitation threshold to a third increased excitation threshold.

Clause 17: The method of any of clauses 1-14, comprising raising the excitation threshold of the nerve or neuron by increasing the intensity of the electrical pulses in two or more steps, wherein each step comprises applying the sub-threshold electrical pulses for a suitable time period to cause an increase in the excitation threshold of the nerve or neuron, thereby increasing the excitation threshold from an initial intensity to an increased intensity, and increasing the sub-threshold electrical pulses to an intensity above the initial intensity and below the increased intensity.

Clause 18: The method of any of clauses 15-17, wherein the time period to cause an increase of the excitation threshold of the nerve or neuron is at least 1 minute, at least 5 minutes, at least 10 minutes, at least 15 minutes, or at least 30 minutes.

Clause 19: The method of any of clauses 1-18, wherein the intensity of the sub-threshold electrical pulses is determined by applying pulses of increasing intensity until a paresthesia sensation is felt by the patient, and the sub-threshold electrical pulses are applied at that intensity, or the electrical pulse intensity is reduced to a maximum level above which the paresthesia sensation is felt, such as 99%, 95%, or 90% of the intensity at which the paresthesia sensation is felt.

Clause 20: The method of any of clauses 1-18, wherein the intensity of the sub-threshold electrical pulses for inducing muscle contractions or a physiological response is determined by applying pulses of increasing intensity until the muscle contraction or the physiological response occurred, and the sub-threshold electrical pulses are applied at a level below that intensity such as 99%, 95%, or 90% of the intensity at which the muscle contraction or the physiological response occurs. (The physiological response can be blood pressure, heart rate, body temperature, or any other autonomic responses.)

Clause 21: The method of any of clauses 1-20, wherein the sub-threshold electrical pulses are stopped for at least 1 minute, 5 minutes, 10 minutes, 15 minutes, or 30 minutes once the nerve block is achieved, wherein during the stop period, the nerve block is maintained. At the end of the stop period, the electrical pulses can be applied again at or below previously stopped intensity without causing nerve excitation to continue the nerve block. The stopping and starting can be repeated to maintain the nerve block for a desired period while saving electrical energy.

Clause 22: An electrical stimulation device comprising a power supply having fixed or adjustable output, one or more conductive leads connected to the power supply, and one or more electrical contacts, such as one or more electrodes, configured to apply sub-threshold electrical pulses according to any of clauses 1-21.

Clause 23: The device of clause 22, having a fixed output with a frequency or frequency range between 1 Hz and 50 kHz, and an output intensity either between 0.01 mA and 10 mA or between 1 and 10,000 mV.

Clause 24: The device of clause 22 or 23, configured as an implantable device, further comprising a power source, such as a battery, and a wired or wireless receiver for receiving control commands from an external computing device and for transmitting status data from the device, such as output frequency, output intensity, output waveform, power source status, stimulation patterns, and/or stimulation history.

Clause 25: The device of clause 22 or 23, configured as an external device to be placed on or near a patient, such as by a strap, hook and loop fastener, belt, or wearable piece of clothing, and further comprising one or more implantable electrodes, separated interface nerve electrodes (SINE), surface electrodes for transferring electrical current to the skin of a patient, or an electromagnet for magnetic neurostimulation.

Clause 26: The device of any of clauses 22-25, comprising a controller and computer-readable instructions for controlling electrical pulse output of the power supply.

Clause 27: The device of any of clauses 22-26, wherein the electrical pulses are biphasic.

Clause 28: The device of clause 27, wherein the biphasic pulses are symmetric between the positive and negative phases of the biphasic pulse.

Clause 29: The device of clause 27, wherein the biphasic pulses are asymmetric between the positive and negative phases of the biphasic pulse.

Clause 30: The device of any of clauses 22-26, wherein the electrical pulses are charge-balanced.

Clause 31: The device of any of clauses 22-30, wherein the electrical pulses have a frequency high enough to change intracellular and extracellular ion concentrations to block nerve conduction or block neuron excitation after applying the pulses for a period of time.

Clause 32: The device of clause 31, wherein the frequency of the electrical pulses is faster than the speed for the sodium-potassium pump of the nerve cell or neuron to recover the intracellular and extracellular ion concentrations that are changed by the electrical pulses.

Clause 33: The device of any of clauses 22-32, wherein the frequency of the electrical pulses is greater than 1 Hz for blocking a nerve.

Clause 34: The device of any of clauses 22-32, wherein the frequency of the electrical pulses is in the range of from 1 Hz to 50 kHz.

Clause 35: The device of any of clauses 22-32, wherein the frequency of the electrical pulses is greater than 1 Hz for blocking a neuron.

Clause 36 The device of clause 35, wherein the frequency of the electrical pulses is in the range of from 1 Hz to 50 kHz.

Clause 37: The device of any of clauses 22-36, wherein the sub-threshold electrical pulses are applied for a time period of at least 1 minute.

Clause 38: The device of clause 37, wherein the sub-threshold electrical pulses are applied for a time period in the range of from 5 minutes to 300 minutes.

Clause 39: The device of clause 37, wherein the sub-threshold electrical pulses are applied for a time period in the range of from 5 hours to 5 days.

Clause 40: The device of any of clauses 22-39, wherein the sub-threshold pulses are applied at an intensity below an initial excitation threshold of the nerve or neuron for a suitable time period sufficient to cause an increase of the excitation threshold of the nerve or neuron to a first increased excitation threshold, and the intensity of the sub-threshold electrical pulses is then raised above the initial excitation threshold of the nerve or neuron and below the first increased excitation threshold of the nerve or neuron and applied for a length of time to further raise the first increased excitation threshold to a second increased excitation threshold.

Clause 41: The device of clause 40, further comprising after raising the first increased excitation threshold to a second increased excitation threshold, raising the intensity of the sub-threshold electrical pulses above the first increased excitation threshold of the nerve or neuron and below the second increased excitation threshold of the nerve or neuron and applied for a length of time to further raise the second increased excitation threshold to a third increased excitation threshold.

Clause 42: The device of any of clauses 22-39, comprising raising the excitation threshold of the nerve or neuron by increasing the intensity of the electrical pulses in two or more steps, where each step comprises applying the sub-threshold electrical pulses for a suitable time period to cause an increase in the excitation threshold of the nerve or neuron, thereby increasing the excitation threshold from an initial intensity to an increased intensity, and increasing the sub-threshold electrical pulses to an intensity above the initial intensity and below the increased intensity.

Clause 43: The device of any of clauses 40-42, wherein the time period to cause an increase of the excitation threshold of the nerve or neuron is at least 1 minute, at least 5 minutes, at least 10 minutes, at least 15 minutes, or at least 30 minutes.

Clause 44: The device of any of clauses 22-43, wherein the intensity of the sub-threshold electrical pulses is determined by applying pulses of increasing intensity until a paresthesia sensation is felt by the patient, and the sub-threshold electrical pulses are applied at that intensity, or the electrical pulse intensity is reduced to a maximum level above which paresthesia sensation is felt, such as 99%, 95%, or 90% of the intensity at which paresthesia sensation is felt.

Clause 45: The device of any of clauses 22-44, wherein the intensity of the sub-threshold electrical pulses for inducing muscle contractions or a physiological response is determined by applying pulses of increasing intensity until the muscle contraction or the physiological response occurred, and the sub-threshold electrical pulses are applied at a level below that intensity such as 99%, 95%, or 90% of the intensity at which the muscle contraction or the physiological response occurs. (The physiological response can be blood pressure, heart rate, body temperature, or any other autonomic responses.)

Clause 46: The device of any of clauses 22-45, wherein the sub-threshold electrical pulses are stopped for at least 1 minute, 5 minutes, 10 minutes, 15 minutes, or 30 minutes once the nerve block is achieved, wherein during the stop period, the nerve block is maintained. At the end of the stop period, the electrical pulses can be applied again at or below the previously stopped intensity without causing nerve excitation to continue the nerve block. The stopping and starting can be repeated to maintain the nerve block for a desired period while saving electrical energy.

Clause 47: The method of any of clauses 1-21, wherein the electrical pulses are produced by a device according to any of clauses 22-46.

Clause 48: Use of an electrical stimulation device comprising a power supply having fixed or adjustable output, one or more conductive leads connected to the power supply, and one or more electrical contacts, such as one or more electrodes, to apply sub-threshold electrical pulses according to any of clauses 1-21 and 47.

Clause 49: A method of blocking a nerve or neuron, comprising: applying an electrical stimulation to the nerve or neuron, wherein the electrical stimulation is of an intensity that does not cause the nerve or neuron excitation for a length of time sufficient to produce a block of nerve conduction or neuron excitation.

Clause 50: The method of clause 49, wherein the intensity of the electrical stimulation is below an initial excitation threshold of the nerve or neuron, optionally wherein the intensity of the electrical stimulation is below a pain threshold.

Clause 51: The method of clause 49 or clause 50, wherein the electrical stimulation is delivered at an intensity of 0.01 mA to 10 mA and/or 1 mV to 10,000 mV.

Clause 52: The method of any of clauses 49-51, wherein the electrical stimulation is delivered at a frequency of 1 Hz to 50 kHz, optionally from 100 Hz to 1.2 kHz.

Clause 53: The method of any of clauses 49-52, wherein the electrical stimulation is delivered for a period of from 100 milliseconds to 14 days, optionally 100 milliseconds to 10 minutes, optionally 1 minute to 14 days, optionally from 30 minutes to 2 hours, optionally from 1 minute to 7 days, optionally from 1 minute to 5 days.

Clause 54: The method of any of clauses 49-53, wherein the electrical stimulation results in the block of nerve conduction or neuron excitation for at least 1 minute following cessation of the electrical stimulation.

Clause 55: The method of any of clauses 49-54, wherein the electrical stimulation comprises biphasic electrical pulses.

Clause 56: The method of any of clauses 49-55, wherein the biphasic pulses are symmetric between the positive and negative phases of the biphasic pulses.

Clause 57: The method of any of clauses 49-56, wherein the biphasic pulses are asymmetric between the positive and negative phases of the biphasic pulse.

Clause 58: The method of any of clauses 49-57, wherein the electrical stimulation comprises electrical pulses that are charge-balanced.

Clause 59: The method of any of clauses 49-58, wherein the electrical stimulation is applied for a time period of at least 5 minutes.

Clause 60: The method of any of clauses 49-59, wherein the stimulation is applied at an intensity below the initial excitation threshold of the nerve or neuron for a length of time sufficient to cause an increase of the initial excitation threshold of the nerve or neuron to a first increased excitation threshold.

Clause 61: The method of any of clauses 49-60, further comprising increasing the intensity of the electrical stimulation to a first increased intensity electrical stimulation above the initial excitation threshold of the nerve or neuron and below the first increased excitation threshold of the nerve or neuron for a length of time sufficient to cause an increase of the first increased excitation threshold of the nerve or neuron to a second increased excitation threshold.

Clause 62: The method of any of clauses 49-61, further comprising increasing the intensity of the first increased intensity electrical stimulation to a second increased intensity electrical stimulation above the first increased excitation threshold of the nerve or neuron and below the second increased excitation threshold of the nerve or neuron for a length of time sufficient to cause an increase of the second excitation threshold of the nerve or neuron to a third increased excitation threshold, and optionally increasing the intensity of the second increased intensity electrical stimulation one or more additional times for a length of time sufficient to further increase the excitation threshold of the nerve or neuron.

Clause 63: The method of any of clauses 49-62, wherein the first increased intensity electrical stimulation and the second increased intensity electrical stimulation have an intensity of 0.01 mA to 10 mA and/or 1 mV to 10,000 mV.

Clause 64: The method of any of clauses 49-63, wherein the first increased intensity electrical stimulation and the second increased intensity electrical stimulation are delivered at a frequency of 1 Hz to 50 kHz, optionally 100 Hz to 1.2 kHz.

Clause 65: The method of any of clauses 49-64, wherein the first increased intensity electrical stimulation, the second increased intensity electrical stimulation, and any additional increased intensity electrical stimulation are delivered for a period of from 100 milliseconds to 14 days, optionally 100 milliseconds to 10 minutes, optionally 1 minute to 14 days, optionally from 30 minutes to 2 hours, optionally from 1 minute to 7 days, optionally from 1 minute to 5 days.

Clause 66: The method of any of clauses 49-65, wherein, as a result of increasing the initial excitation threshold to the first or second or third or any additional increased excitation threshold, the nerve is blocked from conducting action potentials or the neuron is blocked from generating action potentials.

Clause 67: The method of any of clauses 49-66, further comprising, once block of nerve conduction or neuron excitation is achieved, stopping application of the electrical stimulation for a period of at least 1 minute, optionally at least 5 minutes, 10 minutes, 15 minutes, or 30 minutes, wherein the block of nerve conduction or neuron excitation is maintained during the period and, after the period has concluded, resuming electrical stimulation of the nerve or neuron at the same or a lower intensity to continue or prolong the block of nerve conduction or neuron excitation.

Clause 68: The method of any of clauses 49-67, further comprising, once block of nerve conduction or neuron excitation is achieved, maintaining the block by changing the intensity and/or frequency of the electrical stimulation, optionally by reducing the intensity of the electrical stimulation or increasing the frequency of the electrical stimulation.

Clause 69: A device comprising: a controller; a pulse generator in communication with the controller; and an electrode configured to encircle or be placed in contact with a nerve or neuron, the electrode in electrical communication with the pulse generator, wherein the device is configured to apply an electrical stimulation to the nerve or neuron, wherein the electrical stimulation is of an intensity below an initial excitation threshold of the nerve or neuron, optionally wherein the intensity of the electrical stimulation is below a pain threshold of the nerve or neuron, for a length of time sufficient to produce a block of nerve conduction or neuron excitation.

Clause 70: The device of clause 69, wherein the pulse generator is configured to deliver electrical stimulation through the electrode at an intensity of 0.01 mA to 10 mA and/or 1 mV to 10,000 mV.

Clause 71: The device of clause 69 or clause 70, wherein the pulse generator is configured to deliver electrical stimulation through the electrode at frequency of 1 Hz to 50 kHz, optionally 100 Hz to 1.2 kHz for from 100 milliseconds to 14 days, optionally 100 milliseconds to 10 minutes, optionally 1 minute to 14 days, optionally from 30 minutes to 2 hours, optionally from 1 minute to 7 days, optionally from 1 minute to 5 days, wherein the electrical stimulation comprises biphasic, charge-balanced electrical pulses.

Clause 72: The device of any of clauses 69-71, wherein the controller is programmed or configured to instruct the pulse generator to apply electrical stimulation at an intensity below the initial excitation threshold of the nerve or neuron for a length of time sufficient to cause an increase of the initial excitation threshold of the nerve or neuron to a first increased excitation threshold.

Clause 73: The device of any of clauses 69-72, wherein the controller is further programmed or configured to instruct the pulse generator to increase the intensity of the electrical stimulation to a first increased intensity electrical stimulation above the initial excitation threshold of the nerve or neuron and below the first increased excitation threshold of the nerve or neuron for a length of time sufficient to cause an increase of the first increased excitation threshold of the nerve or neuron to a second increased excitation threshold.

Clause 74: The device of any of clauses 69-73, wherein the controller is further programmed or configured to instruct the pulse generator to increase the intensity of the first increased intensity electrical stimulation to a second increased intensity electrical stimulation above the first increased excitation threshold of the nerve or neuron and below the second increased excitation threshold of the nerve or neuron for a length of time sufficient to cause an increase of the second excitation threshold of the nerve or neuron to a third increased excitation threshold, and optionally increasing the intensity of the second increased intensity electrical stimulation one or more additional times for a length of time sufficient to further increase the excitation threshold of the nerve or neuron.

Clause 75: The device of any of clauses 69-74, wherein the controller is programmed or configured to, once block of nerve conduction or neuron excitation is achieved, instruct the pulse generator to stop application of the electrical stimulation for a period of at least 1 minute, optionally at least 5 minutes, 10 minutes, 15 minutes, or 30 minutes, wherein the block of nerve conduction or neuron excitation is maintained during the period and, after the period has concluded, resume electrical stimulation of the nerve or neuron at the same or lower intensity to continue or prolong the block of nerve conduction or neuron excitation.

Clause 76: The device of any of clauses 69-75, wherein the controller is programmed or configured to, once block of nerve conduction or neuron excitation is achieved, instruct the pulse generator to change the intensity and/or frequency of the electrical stimulation, optionally by reducing the intensity of the electrical stimulation or increasing the frequency of the electrical stimulation.

Clause 77: A device comprising: a controller; a pulse generator in communication with the controller; and one or more skin surface electrodes or magnetic coils in electrical communication with the pulse generator, wherein the pulse generator and one or more skin surface electrodes or magnetic coils are configured to apply an electrical stimulation to a nerve or neuron, wherein the electrical stimulation is of an intensity below an initial excitation threshold of the nerve or neuron, optionally wherein the intensity of the electrical stimulation is below a pain threshold of the nerve or neuron, for a length of time sufficient to produce a block of nerve conduction or neuron excitation.

Clause 78: The device of clause 77, wherein the pulse generator is configured to deliver electrical stimulation through the one or more skin surface electrodes or magnetic coils at an intensity of 0.01 mA to 10 mA and/or 1 mV to 10,000 mV.

Clause 79: The device of clause 77 or clause 78, wherein the pulse generator is configured to deliver electrical stimulation through the one or more skin surface electrodes or magnetic coils at frequency of 1 Hz to 50 kHz, optionally 100 Hz to 1.2 kHz for from 100 miiliseconds to 14 days, optionally 100 milliseconds to 10 minutes, optionally 1 minute to 14 days, optionally from 30 minutes to 2 hours, optionally from 1 minute to 7 days, optionally from 1 minute to 5 days, wherein the electrical stimulation comprises biphasic, charge-balanced electrical pulses.

Clause 80: The device of any of clauses 77-79, wherein the controller is programmed or configured to instruct the pulse generator to apply electrical stimulation at an intensity below the initial excitation threshold of the nerve or neuron for a length of time sufficient to cause an increase of the initial excitation threshold of the nerve or neuron to a first increased excitation threshold.

Clause 81: The device of any of clauses 77-80, wherein the controller is further programmed or configured to instruct the pulse generator to increase the intensity of the electrical stimulation to a first increased intensity electrical stimulation above the initial excitation threshold of the nerve or neuron and below the first increased excitation threshold of the nerve or neuron for a length of time sufficient to cause an increase of the first increased excitation threshold of the nerve or neuron to a second increased excitation threshold.

Clause 82: The device of any of clauses 77-81, wherein the controller is further programmed or configured to instruct the pulse generator to increase the intensity of the first increased intensity electrical stimulation to a second increased intensity electrical stimulation above the first increased excitation threshold of the nerve or neuron and below the second increased excitation threshold of the nerve or neuron for a length of time sufficient to cause an increase of the second excitation threshold of the nerve or neuron to a third increased excitation threshold, and optionally increasing the intensity of the second increased intensity electrical stimulation one or more additional times for a length of time sufficient to further increase the excitation threshold of the nerve or neuron.

Clause 83: The device of any of clauses 77-82, wherein the controller is programmed or configured to, once block of nerve conduction or neuron excitation is achieved, instruct the pulse generator to stop application of the electrical stimulation for a period of at least 1 minute, optionally at least 5 minutes, 10 minutes, 15 minutes, or 30 minutes, wherein the block of nerve conduction or neuron excitation is maintained during the period and, after the period has concluded, resume electrical stimulation of the nerve or neuron at the same or a lower intensity to continue or prolong the block of nerve conduction or neuron excitation.

Clause 84: The device of any of clauses 77-83, wherein the controller s programmed or configured to, once the block of nerve conduction or neuron excitation is achieved, instruct the pulse generator to change the intensity and/or frequency of the electrical stimulation, optionally by reducing the intensity of the electrical stimulation or increasing the frequency of the electrical stimulation.

Clause 85: A method of reducing peripheral pain in a patient comprising: applying an electrical stimulation to a peripheral nerve or a group of central neurons, wherein the electrical stimulation is of an intensity that does not cause nerve or neuron excitation for a length of time sufficient to produce a block of nerve conduction or neuron excitation, thereby reducing peripheral pain.

Clause 86: The method of clause 86, wherein the intensity of the electrical stimulation is below an initial excitation threshold of the nerve or neuron, optionally wherein the intensity of the electrical stimulation is below a pain threshold.

Clause 87: The method of clause 85 or clause 86, wherein the electrical stimulation is delivered at an intensity of 0.01 mA to 10 mA and/or 1 mV to 10,000 mV.

Clause 88: The method of any of clauses 85-87, wherein the electrical stimulation is delivered at a frequency of 1 Hz to 50 kHz, optionally 100 Hz to 1.2 kHz.

Clause 89: The method of any of clauses 85-88, wherein the electrical stimulation is delivered for a period of from 100 milliseconds to 14 days, optionally 100 milliseconds to 10 minutes, optionally 1 minute to 14 days, optionally from 30 minutes to 2 hours, optionally from 1 minute to 7 days, optionally from 1 minute to 5 days.

Clause 90: The method of any of clauses 85-89, wherein the stimulation is applied at an intensity below the initial excitation threshold of the nerve or neuron for a length of time sufficient to cause an increase of the initial excitation threshold of the nerve/neuron to a first increased excitation threshold.

Clause 91: The method of any of clauses 85-90, further comprising increasing the intensity of the electrical stimulation to a first increased intensity electrical stimulation above the initial excitation threshold of the nerve or neuron and below the first increased excitation threshold of the nerve or neuron for a length of time sufficient to cause an increase of the first increased excitation threshold of the nerve or neuron to a second increased excitation threshold.

Clause 92: The method of any of clauses 85-91, further comprising increasing the intensity of the first increased intensity electrical stimulation to a second increased intensity electrical stimulation above the first increased excitation threshold of the nerve or neuron and below the second increased excitation threshold of the nerve or neuron for a length of time sufficient to cause an increase of the second excitation threshold of the nerve or neuron to a third increased excitation threshold, and optionally increasing the intensity of the second increased intensity electrical stimulation one or more additional times for a length of time sufficient to further increase the excitation threshold of the nerve or neuron.

Clause 93: The method of any of clauses 85-92, further comprising, once block of nerve conduction or neuron excitation is achieved, stopping application of the electrical stimulation for a period of at least 1 minute, optionally at least 5 minutes, 10 minutes, 15 minutes, or 30 minutes, wherein the block of nerve conduction or neuron excitation is maintained during the period and, after the period has concluded, resuming electrical stimulation of the nerve or neuron at the same or a lower intensity to continue or prolong the block of nerve conduction or neuron excitation.

Clause 94: The method of any of clauses 85-93, further comprising, once block of nerve or neuron excitation is achieved, maintaining the block by changing the intensity and/or frequency of the electrical stimulation, optionally by reducing the intensity of the electrical stimulation or increasing the frequency of the electrical stimulation.

DETAILED DESCRIPTION

Figure 1A:
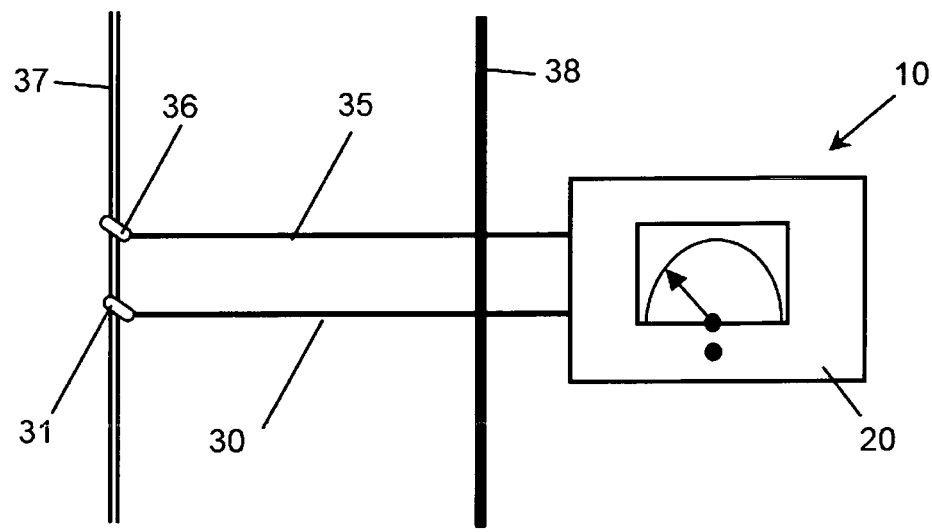
FIGS. 1A-1C are schematic diagrams of various aspects of external systems (FIGS. 1A and 1B), and implantable systems (FIG. 1C) for use in blocking nerves as described herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

The figures accompanying this application are representative in nature, and should not be construed as implying any particular scale or directionality, unless otherwise indicated. For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. Hence, specific dimensions and other physical characteristics related to the embodiments disclosed herein are not to be considered as limiting.

As used herein, the term "comprising" and like terms are open-ended. The term "consisting essentially of" limits the scope of a claim to the specified materials or steps and those that do not materially affect the basic and novel characteristics of the claimed invention. The term "consisting of" excludes any element, step, or ingredient not specified in the claim.

As used herein, the terms "a" and "an" refer to one or more.

As used herein, the term "patient" is any mammal, including humans, and a "human patient" is any human.

As used herein, the terms "communication" and "communicate" refer to the receipt, transmission, or transfer of one or more signals, messages, commands, or other type of data. For one unit or device to be in communication with another unit or device means that the one unit or device is able to receive data from and/or transmit data to the other unit or device. A communication can use a direct or indirect connection, and can be wired and/or wireless in nature. Additionally, two units or devices can be in communication with each other even though the data transmitted can be modified, processed, routed, etc., between the first and second unit or device. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible. Any known electronic communication protocols and/or algorithms can be used such as, for example, TCP/IP (including HTTP and other protocols), WLAN (including 802.11a/b/g/n and other radio frequency-based protocols and methods), analog transmissions, Global System for Mobile Communications (GSM), 3G/4G/LTE, BLUETOOTH, ZigBee, EnOcean, TransferJet, Wireless USB, and the like known to those of skill in the art.

As used herein, the "excitation threshold" of a nerve or neuron is the minimum level to which a neuron and/or nerve membrane must be depolarized to initiate an action potential, resulting in excitation of the nerve or neuron, e.g., initiation of an action potential and propagation of the action potential, and thereby propagation of a signal in the nerve or neuron. The terms "nerve" and "neuron" are used interchangeably herein, particularly with reference to excitation thresholds, though one of skill in the art will appreciate that neuron refers to the cell body at which an action potential is generated and nerve refers to the axon along which an action potential is conducted. One of skill in the art will also appreciate that stimulation parameters sufficient to block excitation in a neuron will be considered suitable to block conduction in a nerve. Depolarization of a nerve or neuron membrane potential results in an increase in the membrane voltage, for example from −70 millivolts (mV) to up to +40 mV.

As used herein, the term "sub-threshold depolarization" or "sub-threshold stimulation" means a stimulation sufficient to increase membrane voltage of a nerve or neuron from resting membrane potential (e.g., −70 mV) to a level below the excitation threshold, such that the nerve or neuron does not become excited, e.g., no action potential is initiated or conducted. It is noted that in the same nerve trunk the motor and sensory nerve fibers have different excitation thresholds; however, in non-limiting embodiments or aspects, an excitation threshold is in the range of −55 mV or −45 mV, all subranges therebetween inclusive. For the same sensory nerve, the excitation thresholds for inducing paresthesia or pain are also different. Therefore, sub-threshold as used herein means that stimulation intensity is below the level to induce muscle contraction, paresthesia, or pain depending on which response (muscle contraction, paresthesia, or pain) is to be blocked. In non-limiting embodiments or aspects, sub-threshold stimulation as described herein increases the membrane voltage from resting (−70 mV) to a voltage less than or equal to −55 mV. Those of skill in the art will appreciate that due to, for example in certain aspects, the use of biphasic pulses of electrical stimulation, the neuron/nerve can be slightly depolarized (below an excitation threshold) and then hyperpolarized.

The "intensity" of an electrical pulse is proportional to, and refers to either the voltage or current (e.g., milliAmperes or mA) applied to the nerve or neuron, with an increased intensity being proportional to an increased voltage or an increased current applied to the nerve or neuron.

In aspects, provided herein is a method of blocking a nerve or neuron in a patient, including applying an electrical stimulation to the nerve or neuron, wherein the electrical stimulation is a sub-threshold stimulation, configured to increase membrane potential of the nerve/neuron from a resting potential, (e.g. −70 mV), to a value less than an excitation threshold of the nerve/neuron for a length of time able to produce a block in the nerve or neuron. As described previously, the excitation threshold for a given nerve/neuron can vary, and those of skill in the art can determine the excitation threshold by applying stimulation of varying intensities, and determining a threshold below which an action potential is not generated or conducted. In non-limiting aspects, the excitation threshold of the neuron is −55 mV, thus, in such aspects, the stimulation increases the membrane potential of the neuron to a value below −55 mV. In aspects, the block induced by the sub-threshold electrical stimulation includes a post-stimulation block.

As used herein, "post-stimulation block" refers to a nerve block that extends past the cessation of the electrical stimulation, and can, depending on the length and intensity of the electrical stimulation, persist from seconds to hours, days, weeks, months, or years, including increments therebetween. In aspects, the post-stimulation block lasts at least 1 minute. In aspects, the post-stimulation block can be maintained after a cessation of stimulation for at least 1 minute, optionally at least 5 minutes, 10 minutes, 15 minutes, or 30 minutes, at which time stimulation can be re-applied. The stimulation that is re-applied can be of an intensity that is higher than an initial intensity that was used to initiate the block, due to the depletion of ions and the increase in excitation threshold achieved through prolonged sub-threshold stimulation, in particular, prolonged sub-threshold stimulation that is applied in a step-wise manner to increase the excitation threshold, as described herein. In aspects, after post-stimulation block is achieved, the frequency and/or intensity of the electrical stimulation can be altered. That is, after achieving post-stimulation block, the frequency of the stimulation can be increased, and/or the intensity of the stimulation can be decreased.

The electrical stimulation can include electrical pulses that can have any suitable characteristic, so long as the stimulation is sub-threshold stimulation. As such, the terms "electrical stimulation" and "electrical pulses" are used interchangeably herein. As will be recognized by a person of skill in the art, characteristics of the electrical pulses, including, without limitation, amplitude (pulse strength, referring to the magnitude or size of a signal voltage or current), voltage, amperage, duration, frequency, polarity, phase, relative timing, and symmetry of positive and negative pulses in biphasic stimulation, and/or wave shape (e.g., square, sine, triangle, sawtooth, or variations or combinations thereof) may be varied in order to provide the desired sub-threshold stimulation and resultant post-stimulation blocking in a patient or class of patients. So long as other characteristics of the electrical signals (e.g., without limitation, amplitude, voltage, amperage, duration, polarity, phase, relative timing and symmetry of positive and negative pulses in biphasic stimulation, and/or wave shape) are within useful ranges, modulation of the pulse frequency will achieve the desired result of sub-threshold induced blocking of a nerve or neuron.

One characteristic of the electrical signals used to produce a desired response, as described above, is the frequency of the electrical pulse. Although effective ranges (e.g., frequencies able to produce a stated effect) may vary from subject-to-subject, and the controlling factor is achieving a desired outcome, certain, non-limiting exemplary ranges may be as follows, with the proviso that the stimulation, or pulses, do not evoke an action potential in the target nerve/neuron or, evoke only a small number of action potentials, such that continued firing of the nerve/neuron is avoided. In aspects, for blocking nerves, useful frequencies range above 1 Hz (Hertz), from approximately 1 Hz to approximately 50 kHz (kilohertz), or from 0.5 kHz to 50 kHz. In aspects, for blocking nerves/neurons, those frequencies range above 1 Hz, from approximately 1 Hz to approximately 50 kHz, or from 0.5 kHz to 50 kHz. In aspects, the range may be more typically from 5 Hz to 10 kHz. In aspects, stimulation is applied at 1 kHz to 4 kHz, all subranges therebetween inclusive. In aspects, stimulation is applied at 1.5 kHz, or 1.2 kHz, or between 100 Hz and 1 kHz, all subranges therebetween inclusive. Data below shows a range of at least from 5 kHz, with 10 kHz pulses being preferred in some instances.

As indicated above, sub-threshold electrical pulses are determined by the intensity of electrical stimulation, which in a medium of stable or relatively stable resistance, such as mammalian tissue, can be characterized as relating to current (I, typically measured in mA), or voltage (V, typically measured in mV), based on Ohm's Law. It should, therefore, be understood that the intensity of the stimulation is a matter of both V and I, and as such, both are increased, e.g., proportionally or substantially proportionally, with increased intensity of stimulation. As such, one characteristic of the pulses is the current that is applied to produce a sub-threshold stimulation that is capable of nerve blocking. Sub-threshold stimulation can be achieved in a typical range of from 0.01 mA to 10 mA. As shown in the examples below, a range of 0.01 mA to 1 mA may be effective in many instances for providing the sub-threshold stimulation. Another characteristic of the pulses are voltage. Sub-threshold nerve stimulation can be achieved in a typical range of from 1 to 10,000 mV, for example, from 100 to 10,000 mV as shown in the examples below. In aspects (described above and in greater detail below) where an excitation threshold is steadily increased by applying a sub-threshold intensity electrical stimulation for a certain period of time until an excitation threshold of a nerve/neuron increases, then the intensity of the stimulation is increased to a higher level, but below the increased excitation threshold, after a certain period of time, a significant post-stimulation block period can be achieved. Breaks, or periods where no electrical stimulation is applied, or is applied less frequently than necessary to achieve the post-stimulation block, can be introduced. Stimulation can then be reintroduced to maintain blockage. In aspects, this reintroduced stimulation can be of a reduced intensity and/or an increased frequency compared to the stimulation required to provide the initial block.

As described herein, the excitation threshold of a nerve or neuron may be increased after a sufficient time period of sub-threshold stimulation, and as such, the limit of the sub-threshold stimulation can increase. That is, while at an initial time point, an increase in membrane voltage potential from −70 mV to −55 mV may be sufficient to depolarize the nerve or neuron and cause an action potential, following exposure of the nerve or neuron to sub-threshold stimulation, the excitation threshold of the nerve can be increased, from −55 mV to −45 mV, or even higher, depending on the duration and intensity of the stimulation. This increase in excitation threshold can be repeated with increasing sub-threshold stimulation, as shown below in the Examples. Accordingly, while a certain I and V may be useful for a first stage of blocking, one or both of I and V can be increased following a sufficient duration sub-threshold stimulation, without concern of causing an action potential to be fired.

As indicated above, the waveform of the pulses may vary, so long as the desired sub-threshold blocking effect is realized. One skilled in the art will appreciate that other types of electrical stimulation may also be used in accordance with the present invention. Monophasic or biphasic stimuli, or a mixture thereof, may be used. Damage to nerves by the application of an electrical current may be minimized, as is known in the art, by application of biphasic pulses or biphasic waveforms to the nerve(s), as opposed to monophasic pulses or waveforms that can damage nerves in some instances of long-term use. "Biphasic current," "biphasic pulses," or "biphasic waveforms" refer to two or more pulses that are of opposite polarity that may be of equal or substantially equal net charge (hence, biphasic and charge balanced), and may be symmetrical, asymmetrical, or substantially symmetrical. This is accomplished, for example, by applying through an electrode one or more positive pulses, followed by one or more negative pulses, typically of the same amplitude and duration as the positive pulses, or vice versa, such that the net charge applied to the target of the electrode is zero, or approximately zero. For charge-balanced biphasic stimulation, the opposite polarity pulses may have different amplitudes, profiles, or durations, so long as the net applied charge by the biphasic pulse pair (the combination of the positive and negative pulses) is approximately zero.

The waveform may be of any useful shape, including without limitation: sine, square, rectangular, triangular, sawtooth, rectilinear, pulse, exponential, truncated exponential, or damped sinusoidal. The pulses may increase or decrease over the stimulation period. In aspects, the waveform is rectangular. The pulses may be applied continuously or intermittently as needed. As indicated below, stimulation of a nerve or neuron at certain voltages or currents for certain time periods elicits post-stimulation nerve blockage. Therefore, the stimulation may be applied for short intervals (e.g., 1-10 minutes) or longer intervals (360 minutes or even longer, for example days, weeks, months, or even years) to achieve longer-lasting blockage/relief, in terms of hours, days, weeks, months, or years. In aspects, the stimulation is applied for at least 5 minutes. In aspects, the stimulation is applied for 30 minutes to 2 hours, all subranges therebetween inclusive. In certain aspects, the stimulation is applied for at least 70 minutes, at least 80 minutes, or at least 90 minutes. In aspects, the pulses are applied for from 100 miiliseconds to 14 days, optionally 100 milliseconds to 10 minutes, optionally 1 minute to 14 days, optionally from 30 minutes to 2 hours, optionally from 1 minute to 7 days, optionally from 1 minute to 5 days, all subranges therebetween inclusive. As described above, the stimulation may be applied intermittently (that is, the pulses are turned on and off alternately during a stimulation interval for any time period) during continuous or interval stimulation protocols. For example, the stimulation may be applied for 5 seconds on and 5 seconds off over an interval of, for example, 1-10 minutes or longer (e.g., hours, days, weeks, months, years). Other examples of intermittent application of pulses may be 1-90 seconds on and 1-90 seconds off over up to a 360 minute time period. So long as other pulse parameters are within acceptable limits, the inhibition is temporary and does not damage the involved neurons/nerves. For example, intermittent application of pulses may be continuous, that is, for as long as the pulses are having the desired effect, and for as long as the patient desires (i.e., is not painful or harmful to the patient). In one aspect, the stimulation is provided continuously, for example, to treat severe symptoms, or any symptom that does not respond to intermittent, short-term stimulation to the degree desired by a clinician or the patient.

In aspects, as described above and demonstrated below, a sub-threshold electrical stimulation is applied to a nerve or neuron for a suitable length of time so that the excitation threshold intensity of the nerve or neuron increases. As such, after application of a sub-threshold electrical pulse of sufficient duration, the intensity of the electrical pulse can be increased in a stepwise fashion above the initial threshold intensity, but below the newly increased threshold intensity.

Suitable lengths of time are greater than one minute (compare, Miles, J. D., et al. Effects of ramped amplitude waveforms on the onset response of high-frequency mammalian nerve block (2007) *J. Neural Eng.* 4 (2007) 390-398, where voltage applied to nerves was ramped from 0V to 10V over time, with steps ranging in duration of from 100 nanoseconds to 60 seconds, and finding such ramping parameters were unable to prevent onset response), including greater than 2, 3, 4, 5, 6, 7, 8, 9, 10, or 15 minutes, including increments therebetween, and in aspects, greater than 2 minutes, greater than 5 minutes, and greater than 10 minutes. In non-limiting embodiments or aspects, the steps for incrementally increasing excitation threshold can be of a duration in the range of hours, for example, and without limitation, 1 hour, 2 hours, 3 hours, or more.

In aspects, the excitation threshold can be repeatedly increased to provide long-lasting block of the neuron and/or nerve. In aspects, the stimulation is applied at an intensity below an initial excitation threshold of the neuron (e.g., below −55 mV) for a time sufficient to cause an increase of the initial excitation threshold of the neuron to a first increased excitation threshold (e.g. >−55 mv). Thereafter, a first increased intensity electrical stimulation configured to increase the membrane potential of the neuron higher than the initial excitation threshold of the neuron and below the first increased excitation threshold of the neuron can be applied. This first increased intensity electrical stimulation can be applied for a time sufficient to cause an increase of the first increased excitation threshold of the neuron to a second increased excitation threshold. Thereafter, a second increased intensity electrical stimulation can be applied to the neuron, wherein the second increased intensity electrical stimulation is configured to increase the excitation threshold of the neuron higher than the first increased excitation threshold of the neuron and below the second increased excitation threshold of the neuron. The second increased intensity electrical stimulation can be applied for a time sufficient to cause an increase of the second excitation threshold of the neuron to a third increased excitation threshold. This process can be repeated any number of times. Without wishing to be bound by the theory, it is believed that long-term block can be achieved through such a step-wise increase in excitation threshold because of the significant reconfiguration of ion concentrations (e.g., sodium and potassium) between intracellular and extracellular compartments.

As a non-limiting aspect, where the excitation threshold is 1 mA at 1 kHz, biphasic pulses, a sub-threshold current of 0.9 mA is applied for a suitable length of time, such as for 30 minutes to 2 hours, at which time the excitation threshold increases to 2 mA. At that time, the sub-threshold current is raised to 1.9 mA and is applied for a suitable length of time to further increase the excitation threshold, such as for 30 minutes to 2 hours, at which time the excitation threshold increases to 5 mA. The step-wise increase in excitation threshold can be repeated until a nerve block, including, in aspects, a post-stimulation nerve block, which can persist beyond cessation of stimulation, of a desired length is achieved.

The timeframe on which the excitation threshold can be increased (e.g., in a step-wise fashion) can vary. In aspects, the increase (e.g., each step) can occur quickly, for example and without limitation on the millisecond scale (1 millisecond, 10 milliseconds, 100 milliseconds, and all ranges therebetween), with the proviso that because of the rapid nature of the increase, the increase in intensity is small (e.g., on the µA scale, such as 10 µA). In aspects, the duration of steps increases with time, for example, steps can be of 1 ms, 10 ms, 100 ms, 1 s, 10 s, 1 min, 10 min, 30 min, hour(s), day(s), week(s), month(s), year(s), etc.

In aspects, also provided herein is a method of treating, reducing, or eliminating pain in a patient, including applying an electrical stimulation to a nerve or neuron, wherein the electrical stimulation is a sub-threshold stimulation, configured to increase membrane potential of the neuron from a resting potential, (e.g. −70 mV), to a value less than an excitation threshold of the neuron for a length of time able to produce a block, in some aspects a post-stimulation block, in the nerve or neuron, thus reducing or eliminating pain. In aspects, the pain is from a limb, and the method includes stimulating a neuron (centrally) or a nerve (peripherally) innervating that limb. In aspects, in a patient experiencing phantom pain from an amputated limb, sub-threshold electrical pulses are applied to one or more nerves that would otherwise innervate the missing limb. In one aspect, sub-threshold electrical pulses are applied at a single intensity to achieve the nerve block, that is, loss of phantom pain. In another aspect, the sub-threshold electrical pulses are applied in a step-wise increasing fashion as described above, until nerve block is achieved, that is, pain is lost. In aspects, the sub-threshold electrical pulses described herein may or may not cause a paresthesia sensation in the patient. In aspects, the patient may experience some paresthesia effects when the sub-threshold electrical pulses are applied in any manner, e.g., constant or step-wise increasing, but the patient does not experience acute muscle spasticity or pain associated with typical onset response.

In practice, the sub-threshold electrical pulse can be applied to a nerve of a patient, and can be increased until paresthesia is experienced and then either decreased slightly to remove the paresthesia effect, or if tolerable, the electrical pulse is not reduced and is continued until paresthesia effect disappears. When paresthesia is present, it may disappear after a sufficient length of time of stimulation, and that event can be used as a signal, e.g., to a patient and/or to a clinician, that the sub-threshold block is effective, and the intensity of the applied current can be increased until paresthesia is again experienced. Alternatively, the applied current can be increased step-wise after a suitable time has passed, such as 5, 10, 15, 20, 25, 30, 45, or 60 minutes, or increments therebetween. The step-wise increasing of sub-threshold electrical pulses can be continued until nerve block is achieved, corresponding to a loss of pain, such as loss of phantom pain, at which time the blocking current is optionally maintained for a suitable length of time ranging from minutes (e.g., five, ten, 15, 20, 30, 45, or 60 minutes), to hours (e.g., two, four, six, 12, or 24 hours), to days or even weeks, months, or years.

In non-limiting embodiments or aspects, the described sub-threshold blocking method results in a post-stimulation block, meaning that once a blockage is achieved, the blocking electrical pulses can be stopped for a length of time, and re-initiated at full blocking intensity, without need for the step-wise increase of stimulation. As such, after initial stimulation, blocking electrical pulses, e.g., at full blocking intensity, can be applied periodically to maintain the block, for example, once every hour for two to 15 minutes, or 15 minutes on and 15 minutes off. Suitable and optimal blocking timing parameters can be determined case-by-case, especially considering that each individual, nerve, neuron, stimulation device, and stimulation parameter, are likely to dictate how often each application of the blocking pulses is applied and for how long they are applied.

Turning to the figures, also provided herein are devices for applying sub-threshold stimulation in a manner sufficient to induce post-stimulation nerve/neuron block. FIG. 1A provides a general schematic of one non-limiting embodiment or aspect of an electrical stimulation device 10 useful in aspects of the methods described herein. The device 10 includes a power supply or pulse generator 20. The power supply/pulse generator 20 may be fixed output, or may be adjustable, for example within a useful range as described herein. The device 10 includes a first conductive lead 30 and a first nerve cuff 31, and a second conductive lead 35 with a second nerve cuff 36. The conductive leads 30 and 35 can be combined into a single lead to connect the nerve cuffs 31 and 36. In embodiments (not shown), the nerve cuffs 31 and 36 can also be combined into a single cuff, or they can be completely eliminated and replaced by conductive metals/electrodes located on the lead 30 and 35 or located on the single lead that combines both 30 and 35. Conductive leads 30, 35 can be directly wired to power supply/pulse generator 20, or may each comprise multiple leads and electrical connectors, fasteners, terminals, or clips to produce a contiguous electrical connection between the power supply/pulse generator 20 and the respective nerve cuffs. A nerve 37 also is depicted. Skin 38 is also shown, and as such the device 10 is external and can be a hand-held or body-worn device held in place by a belt or strap, such as by a hook and loop fastener band, though in aspects, the device 10 can be an implantable device (described in more detail below). In FIG. 1A, the leads are of opposite polarity and, together, form a circuit for application of any electrical waveform described herein. Alternative designs, with different leads, probes, electrodes, or electrical contacts, or combinations thereof will be apparent to those of ordinary skill. As used herein, an "electrical contact" is inclusive of any structure useful for directly applying an electrical current to a nerve or tissue in a patient, such as to the skin of a patient. Structures for producing a magnetic field, and therefore an electrical current via induction, are not considered to be electrical contacts. Nevertheless, in aspects, induction probes, that is structures capable of generating a magnetic field capable of producing an electrical current, may be used to produce the electrical pulses described herein.

Figure 1B:
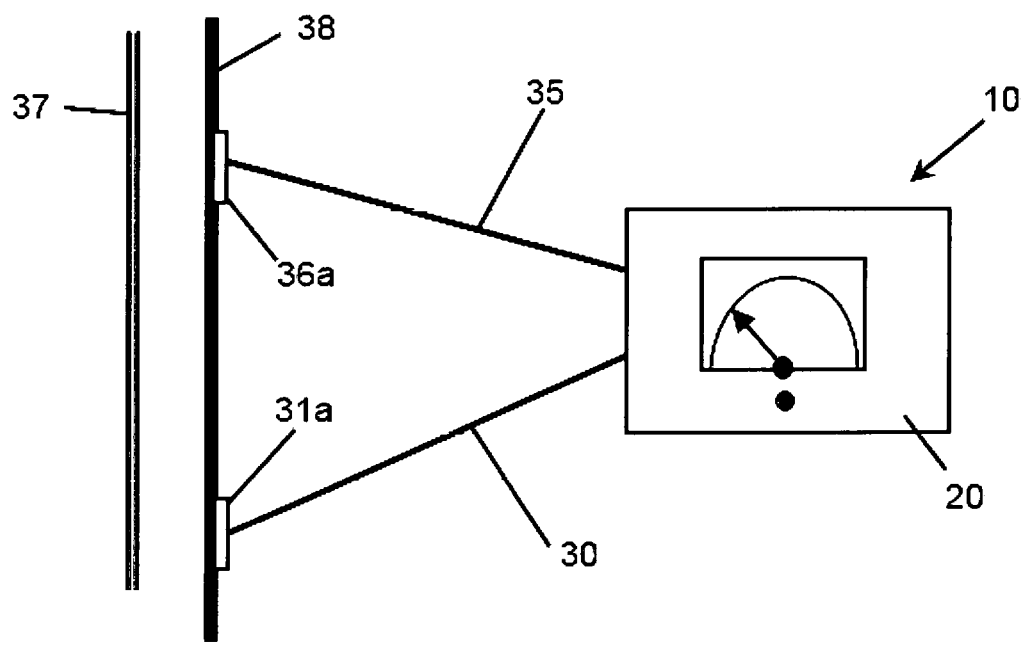

FIG. 1B depicts schematically another aspect of a device 10 for nerve block, which, like the device of FIG. 1A, has an external power supply. In FIG. 1B, like reference numbers as compared to reference numbers of FIG. 1A, refer to like elements of the device 10. However, surface electrodes 31a and 36a replace nerve cuffs 31 and 36 of FIG. 1A, and stimulation is transcutaneous. In an alternative aspect, not shown, surface electrodes 31a and 36a are replaced by electromagnets for magnetic induction stimulation of impulses in nerve 37.

Figure 1C:
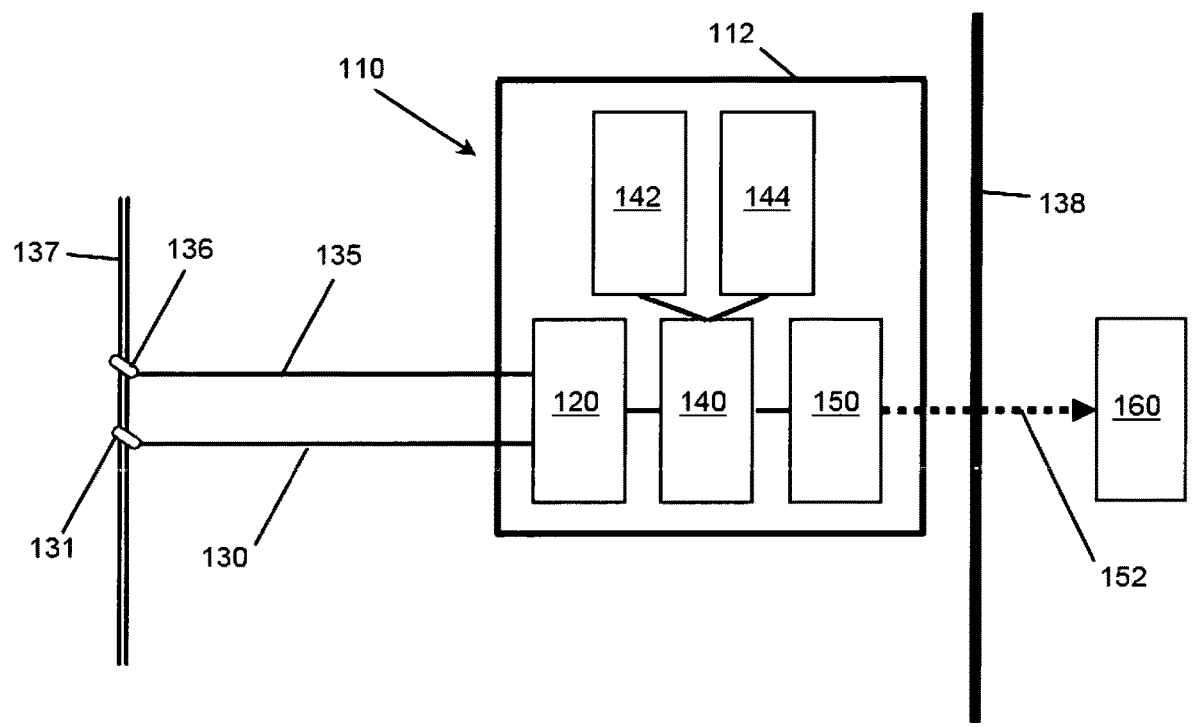

FIG. 1C depicts a further aspect of the nerve block device 110 that is implanted, and includes an implantable housing 112. The housing 112 contains various subunits of the device, including a power supply/pulse generator 120 connected to a first lead 130 connected to a first nerve cuff 131, and a second lead 135 connected to a second cuff 136 for stimulating a nerve 137. Skin 138 is depicted for context. The conductive leads 130 and 135 can be combined into a single lead to connect the nerve cuffs 131 and 136. As described above, in aspects (not shown), the nerve cuffs 131 and 136 can also be combined into a single cuff, or they can be completely eliminated and replaced by conductive metals/electrodes located on the lead 130 and 135 or located on the single lead that combines both 130 and 135. For monopolar stimulation, one of the cuff/electrode can be located on the housing 112. The housing may be composed of any biocompatible material as are known in the medical fields for use in such implantable devices, such as a plastic, metal, carbon fiber, or ceramic material, or a polymer-coated material, such as a metal or plastic housing coated with a biocompatible polymer or hydrogel. The housing 112 also contains various connected subunits of the device 110, including a processor 140, a storage module 142 including transient data storage (e.g., RAM), and non-transient data storage, such as flash memory or a solid-state drive, and a battery 144 that is optionally rechargeable by magnetic induction. The processor 140 can also be connected to a wireless communications module 150 for communicating wirelessly, e.g., by near-field communication, or by BLUETOOTH, Wi-Fi, or over a cellular network, with an external computer or computer network, such as a smartphone, tablet, laptop, personal computer, smart watch, workstation, server, or computer network.

The devices of FIGS. 1A-1C can be battery-powered, and optionally the battery is rechargeable. Where the device is implanted, the device can be recharged by wireless, e.g., magnetic induction recharging methods, as are known. The devices of FIG. 1A and/or FIG. 1B also can include a communications interface, such as a wireless communications interface or module, for transmitting data, and for receiving instructions from a separate computing device, such as from a controller app or software on a smartphone, tablet, laptop, personal computer, workstation, server, or computer network. As would be appreciated by those of ordinary skill in the fields of computer and software engineering, a multitude of potential device and system configurations and implementation schemes can be used to control devices and systems that provide electrical stimulation and nerve block as described herein.

Referring to FIG. 1C, but equally applicable to any aspect of the device, e.g., device 10 of FIG. 1A and/or FIG. 1B, the device 110 comprises a controller for executing functions related to electrical pulse output of the power supply. In some examples, a controller is a central processing engine including a baseline processor, memory, and communications capabilities. For example, the controller can be any suitable processor comprising computer readable memory and configured to execute instructions either stored on the memory or received from other sources. Computer readable memory can be, for example, a disk drive, a solid-state drive, an optical drive, a tape drive, flash memory (e.g., a non-volatile computer storage chip), cartridge drive, and control elements for loading new software.

In some examples, the controller includes a program, code, a set of instructions, or some combination thereof, executable by the processor for independently or collectively instructing the device to interact and operate as programmed, referred to herein as "programming instructions". In some examples, the controller is configured to issue instructions to the power supply/pulse generator to initiate sub-threshold electrical pulses, and to control output parameters of the power supply in a manner sufficient to induce nerve/neuron block, in aspects post-stimulation block, as described throughout this disclosure (e.g., sub-threshold stimulation, repeatedly increasing stimulation to increase excitation thresholds, and the like). Those of skill in the art will appreciate that a processor associated with a device 10, 110 disclosed herein can be programmed to deliver suitable sub-threshold stimulation as described generally throughout this disclosure. In any case, the controller is configured to receive and process electrical pulse parameters, either programmed into the device or from an external source, and optionally to output data obtained from the power supply as feedback to determine if the power supply is producing a desired output. Processing can include applying filters and other techniques for removing signal artifacts, noise, baseline waveforms, or other items from captured signals to improve readability.

Further to the above, the device 10, 110 can include programming instructions that, when executed by the processor 140, cause the power supply/pulse generator 120 to apply electrical stimulation at an intensity below an initial excitation threshold of the neuron (e.g., below −55 mV) for a time sufficient to cause an increase of the initial excitation threshold of the neuron to a first increased excitation threshold (e.g. >−55 mv). These parameters are described above, but can include stimulation at from 1 Hz to 50 kHz, at an intensity of 0.01 mA to 10 mA and/or from 1 mV to 10,000 mV, for a duration of seconds to days, all subranges therebetween inclusive for all parameters.

As also described previously, the processor 140 can thereafter instruct the power source/pulse generator 120 to apply a first increased intensity electrical stimulation configured to increase the excitation threshold of the neuron higher than the initial excitation threshold of the nerve/neuron and below the first increased excitation threshold of the nerve/neuron. This first increased intensity electrical stimulation can be applied for a time sufficient to cause an increase of the first increased excitation threshold of the nerve/neuron to a second increased excitation threshold. Thereafter, the processor 140 can instruct the power supply/pulse generator 120 to apply a second increased intensity electrical stimulation to the nerve/neuron, wherein the second increased intensity electrical stimulation is configured to increase the excitation threshold membrane potential of the nerve/neuron higher than the first increased excitation threshold of the nerve/neuron and below the second increased excitation threshold of the nerve/neuron. The second increased intensity electrical stimulation can be applied for a time sufficient to cause an increase of the second excitation threshold of the nerve/neuron to a third increased excitation threshold. Having a device 10, 110 programmed or configured in this way improves the functioning of the device over that of past devices, which, as described previously, apply super-threshold stimulation which can be, at a minimum, uncomfortable/inconvenient, and can be unduly pain-inducing. In aspects, the controller can be programmed or configured to, once block of nerve conduction or neuron excitation is achieved, instruct the pulse generator to change the intensity and/or frequency of the electrical stimulation, optionally by reducing the intensity of the electrical stimulation or increasing the frequency of the electrical stimulation. Various sensors and devices can be utilized to determine whether block has been achieved. For example, as described above and illustrated in the examples below, a device can include more than one contact, lead, or cuff. In aspects, one of the contacts/leads/cuffs can be located proximally of the blocking contact/lead/cuff, and blocking can be determined by whether a stimulation pulse applied proximally of the block results in transmission of an action potential distally of the location of the blocking contact/lead/cuff.

The following illustrative examples show that prolonged high-frequency (kHz) biphasic stimulation (HFBS) at a sub-threshold intensity can block nerve conduction by slowly changing ion concentrations within nerves to be blocked.

Example 1—Post-Stimulation Nerve Block Induced by HFBS

Figure 2:
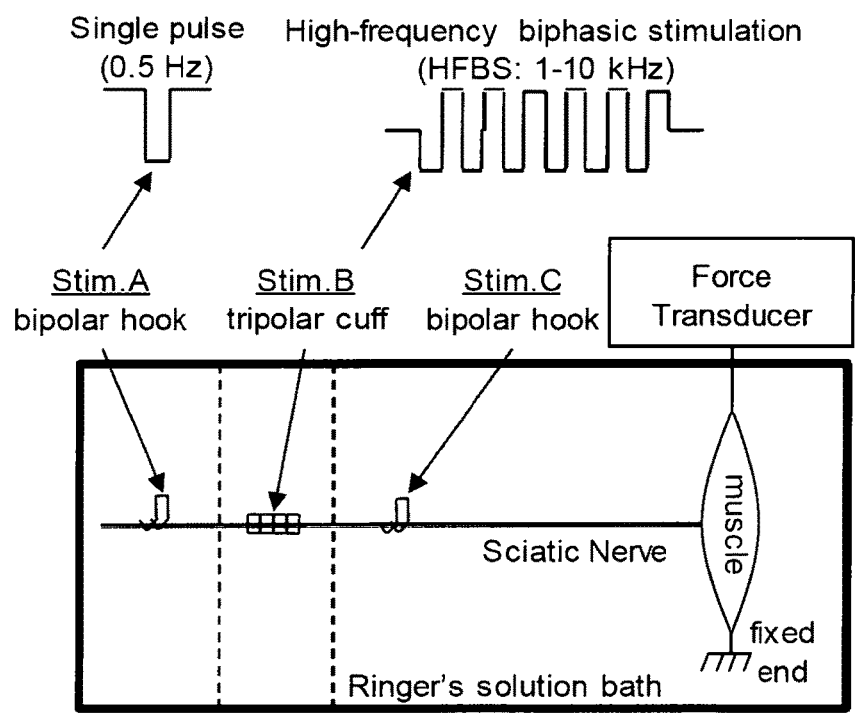
FIG. 2 shows a frog sciatic nerve-muscle preparation.

FIG. 2 shows that the isolated sciatic nerve is stimulated by a bipolar hook electrode (Stim.A=0.5 Hz single pulses) and blocked by a tripolar cuff electrode (Stim.B=1-10 kHz HFBS). The frog sciatic nerve-muscle preparation is immersed in Ringer's solution in a bath.

Figure 3:
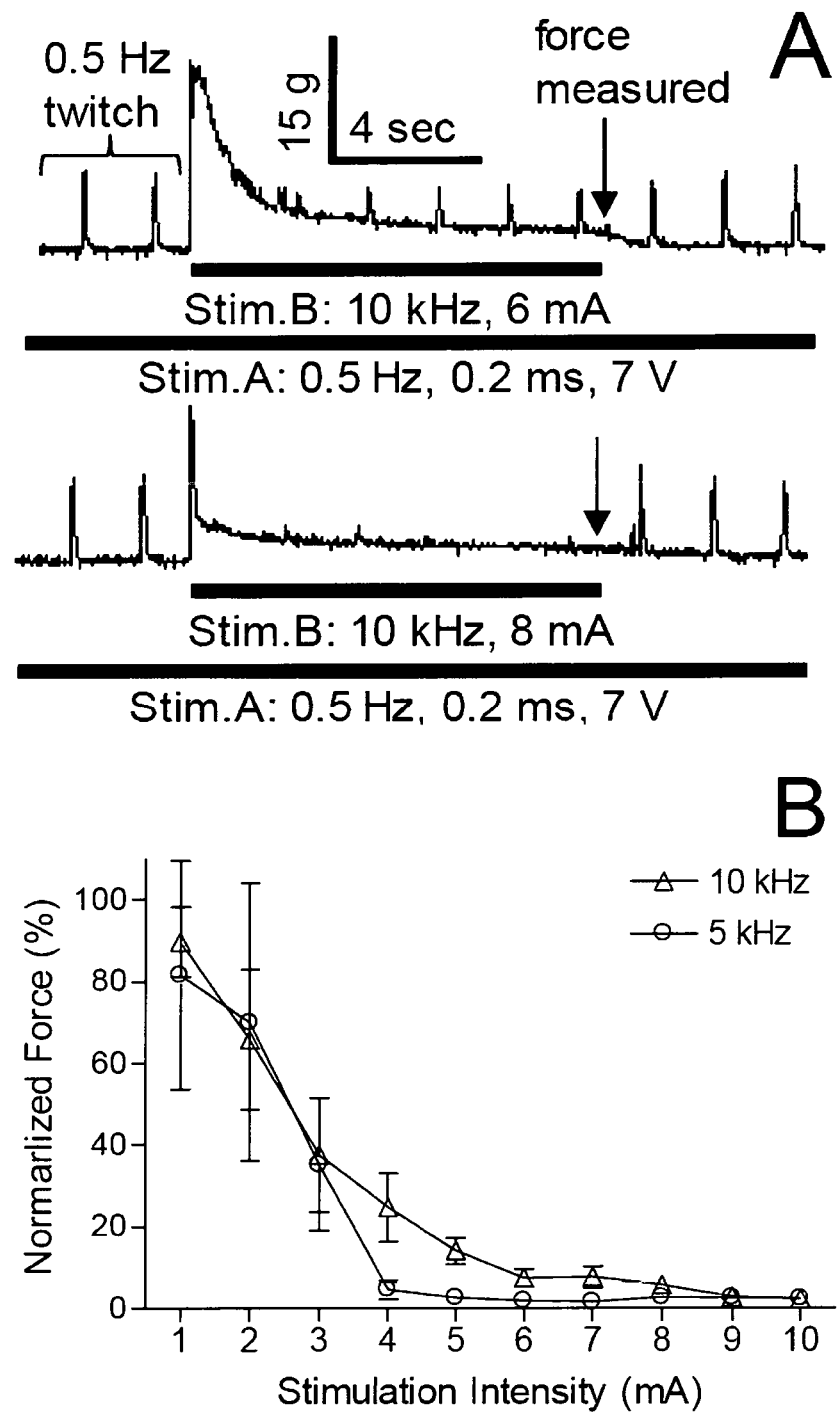
FIG. 3 shows intensity-dependent block of muscle twitching by high-frequency biphasic stimulation (HFBS), with stimulation duration indicated by the black bars.
Figure 4:
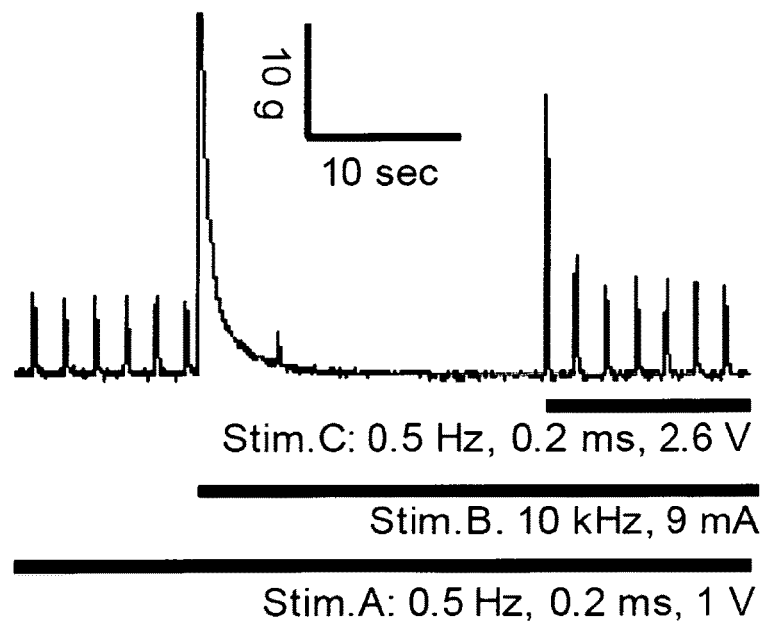
FIG. 4 shows HFBS block localized at the HFBS electrode site.

The 10 kHz HFBS at low intensity (1-6 mA) induces a strong muscle contraction that is reduced and becomes an initial muscle twitch as the HFBS intensity increases to a higher level (8-10 mA) (see FIG. 3, panel A). The muscle contraction force measured at the end of HFBS indicates that a complete nerve block occurs at a minimal intensity (i.e., the block threshold) between 4-6 mA for 5-10 kHz HFBS (FIG. 3, panel B). However, the 10 kHz requires slightly higher stimulation intensity than 5 kHz to block the 0.5 Hz muscle twitching induced by Stim.A (FIG. 3, panel B). In FIG. 3, the forces measured at the end of HFBS were normalized to the maximal response during each experimental trial. After Stim.B completely blocked the muscle twitching induced by Stim.A, Stim.C at a site distal to Stim.B still induced muscle twitching (FIG. 4) indicating that the nerve block occurs locally at the Stim.B electrode, excluding the possibility of a neuromuscular junction block. After termination of a 10 second HFBS, the nerve conduction recovered quickly and the muscle twitching induced by 0.5 Hz Stim.A reappeared within seconds (FIG. 3, panel A), that is, post-stimulation block was not observed.

Figure 5:
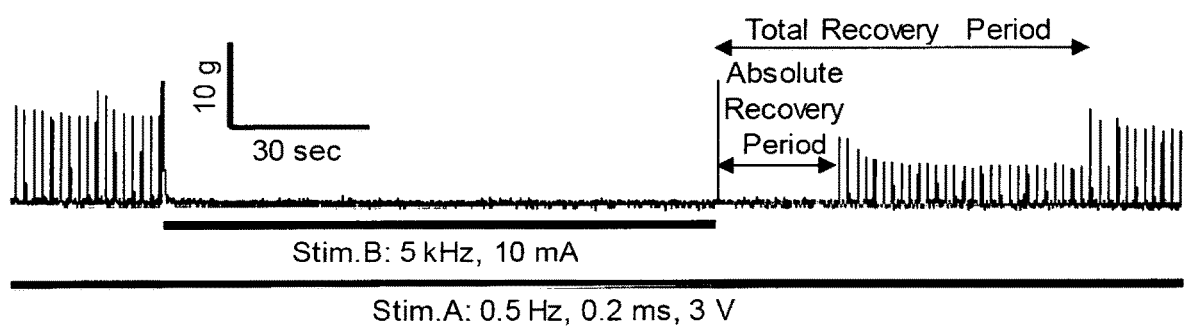
FIG. 5 shows recovery of the muscle twitching response after a long duration (2 minutes) HFBS, with stimulation duration is indicated by the black bar.
Figure 6:
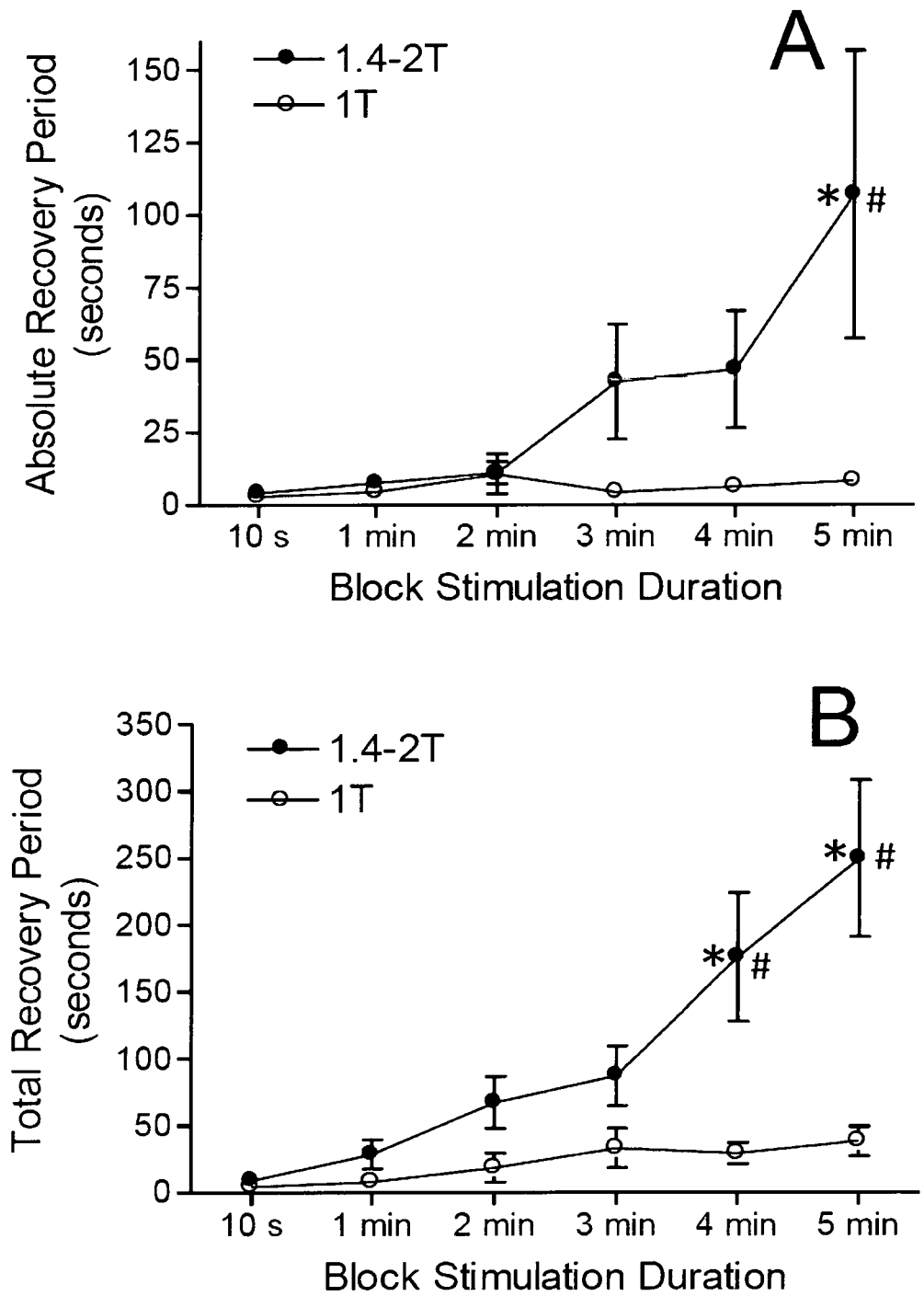
FIG. 6 shows that the duration of post-stimulation block are dependent on the intensity and duration of the high-frequency biphasic stimulation. * significantly different by one-way ANOVA; # significantly different by two-way ANOVA.

However, post-stimulation block was observed when the HFBS lasted more than 10 seconds (FIG. 5). After terminating the HFBS, the recovery of nerve conduction consisted of two distinct periods. During the first period, a complete block was maintained and no muscle twitching could be induced by 0.5 Hz Stim.A. This period is termed the absolute recovery period (FIG. 5). During the second period, the muscle twitching induced by 0.5 Hz Stim.A partially recovered (FIG. 5). The total recovery period is defined as the post-stimulation duration required for the muscle twitching response to recover about 95% of pre-stimulation level (FIG. 5). It is worth noting that the recovery occurred abruptly (see FIG. 5) in 13 out of 16 animals. The duration of post-stimulation block is proportional to the stimulation duration and intensity (FIG. 6).

Example 2—Mechanisms Underlying Acute HFBS Block Revealed by Model Analysis

Figure 7:
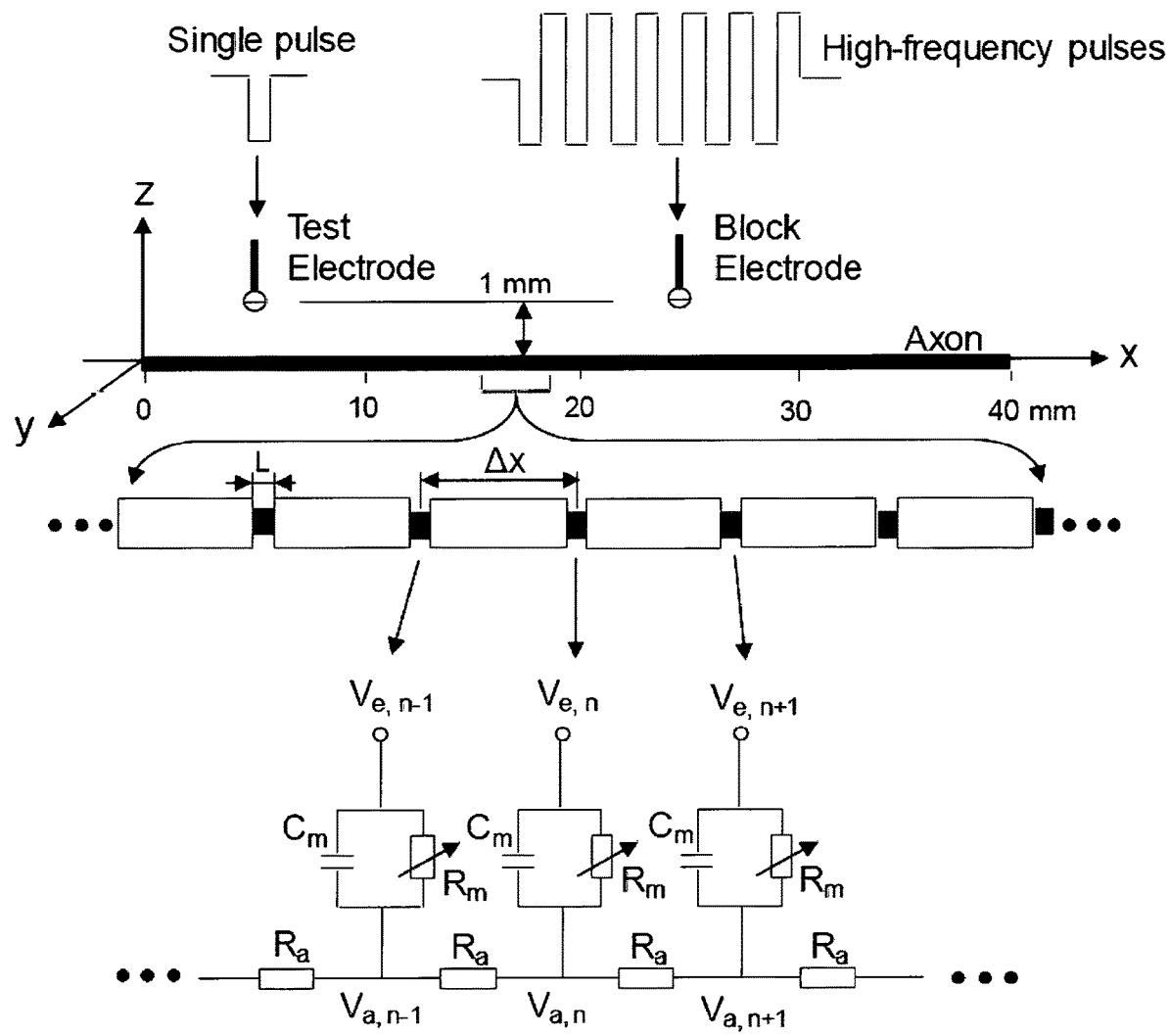
FIG. 7 shows a frog myelinated axon model (Frankenhaeser-Huxely model) to simulate conduction block induced by high-frequency biphasic stimulation.

FIG. 7 shows that a 40 mm long myelinated axon is modeled with the inter-node length $\Delta x=100d$ (where d is the axon diameter). Each node (nodal length L=2.5 μm) is modeled by a membrane capacitance (Cm) and a variable membrane resistance (Rm). Two monopolar point electrodes (with the indifferent electrode at infinity) are placed at 1 mm distance to the axon. One is the block electrode at the 25 mm location along the axon, where the HFBS will be delivered. The other is the test electrode at the 5 mm location, which delivers a monophasic single pulse (pulse width 0.1 ms at a range of intensities from 0.5 mA to 2 mA) to evoke an action potential and test whether this action potential can propagate through the site of the block electrode. The test electrode is always a cathode (negative pulse), and the block electrode always delivers biphasic pulses with the cathodal phase first.

We assume that the axon is in an infinite homogeneous medium (resistivity $\rho_e=300$ Ωcm). After neglecting the small influence induced by the presence of the axon in the homogeneous medium, the extracellular potential $V_{e,n}$ at the $n^{th}$ node along the axon can be calculated by:

$$V_{e,n}(t) = \frac{\rho_e}{4\pi}\left[\frac{I_{block}(t)}{\sqrt{(n\Delta x - x_0)^2 + z_0^2}} + \frac{I_{rest}(t)}{\sqrt{(n\Delta x - x_1)^2 + z_1^2}}\right]$$

where $I_{brock}(t)$ is the HFBS current delivered to the block electrode (at location $x_0$=25 mm, $z_0$=1 mm); $I_{rest}(t)$ is the single test pulse delivered to the test electrode (at location $x_1$=5 mm, $z_1$=1 mm). The change of the membrane potential $V_n$ at the $n^{th}$ node is described by:

$$\frac{dV_n}{dt} = \left[\frac{d\Delta x}{4\rho_i L}\left(\frac{V_{n-1} - 2V_n + V_{n+1}}{\Delta x^2} + \frac{V_{e,n-1} - 2V_{e,n} + V_{e,n+1}}{\Delta x^2}\right) - I_{i,n}\right]/C_m$$

where $V_n = V_{a,n} - V_{e,n} - V_{rest}$; $V_{a,n}$ is the intracellular potential at the $n^{th}$ node; $V_{e,n}$ is the extracellular potential at the $n^{th}$ node; $V_{rest}$ is the resting membrane potential; $\rho_i$ is the resistivity of axoplasm (100 Ωcm); $C_m$ is the capacity of the membrane (2 $\rho F/cm^2$); is the ionic current at the nth node described by Frankenhaeuser-Huxley equations. The parameters describing the ionic current $I_{i,n}$ can be found in previous studies. The model was solved by the Runge-Kutta method with a time step of 0.001 ms and initial condition $V_n$=0. Sealed boundary conditions (no longitudinal currents) at the two ends of the modeled axon were used. The simulation can be performed at a temperature between 15° C. and 37° C. by setting the temperature parameter in this axonal model.

Figure 8:
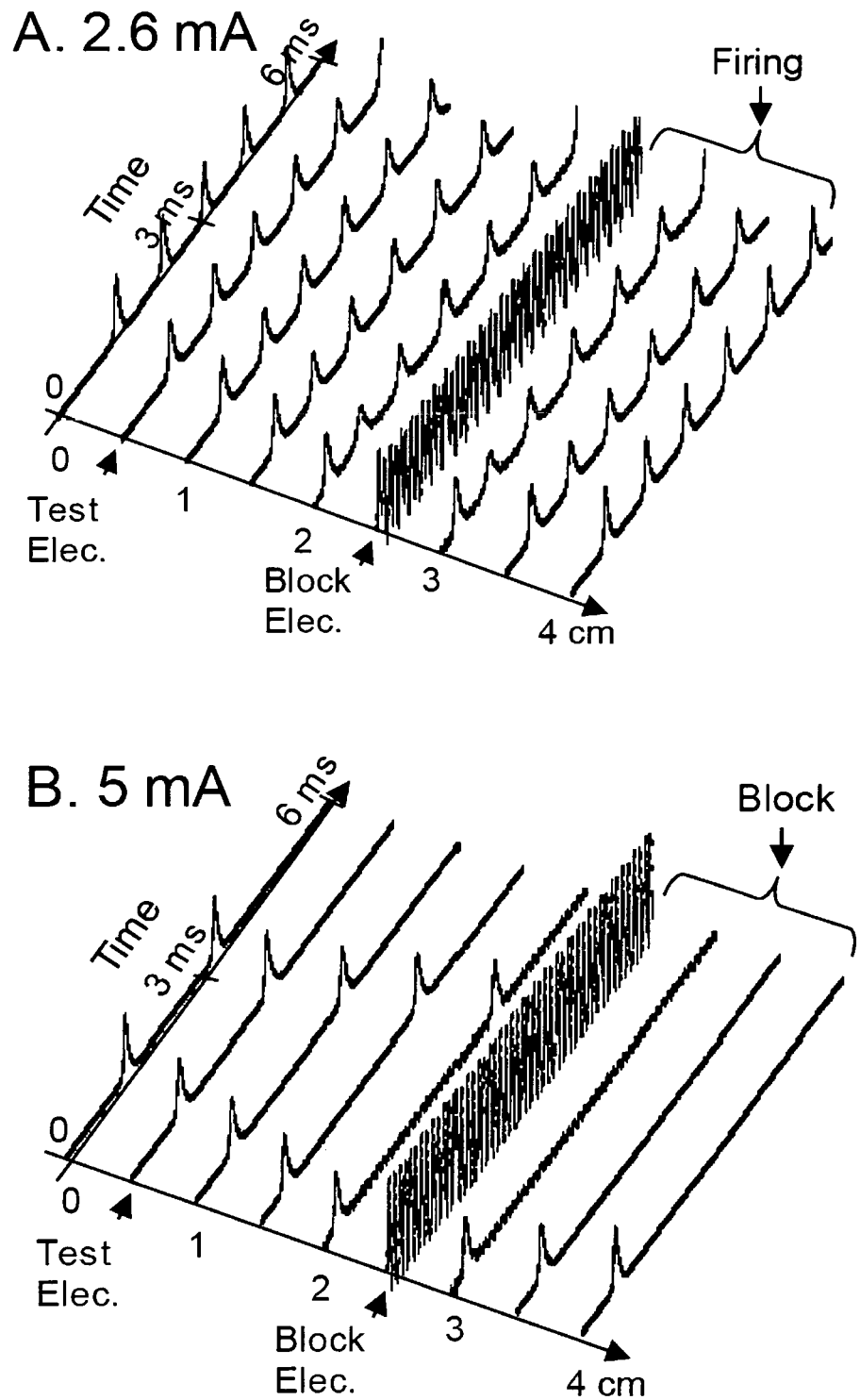
FIG. 8 shows propagation of action potentials along the axon induced by high-frequency biphasic stimulation at different intensities. A. 2.6 mA; B. 5 mA. Stimulation: 8 kHz. Axon diameter: 5 μm. Temperature: 37° C.

FIG. 8 shows a typical nerve firing pattern and conduction block induced by HFBS that were simulated by the myelinated axon model as shown in FIG. 7. At a low intensity (2.6 mA), the HFBS caused repetitive firing of action potentials (FIG. 8, panel A), but only an initial action potential was induced at a higher intensity (5 mA, FIG. 8, panel B). The test pulse was applied by the test electrode at 3 ms after the HFBS started in FIG. 8, panel B, but was not applied in FIG. 8, panel A. The test pulse generated an action potential propagating toward the block electrode, and the HFBS (8 kHz) successfully blocked the propagation of an action potential at the block electrode (FIG. 8, panel B). These simulation results agree very well with the results obtained from frog sciatic nerve-muscle preparation as shown in FIG. 3.

Figure 9:
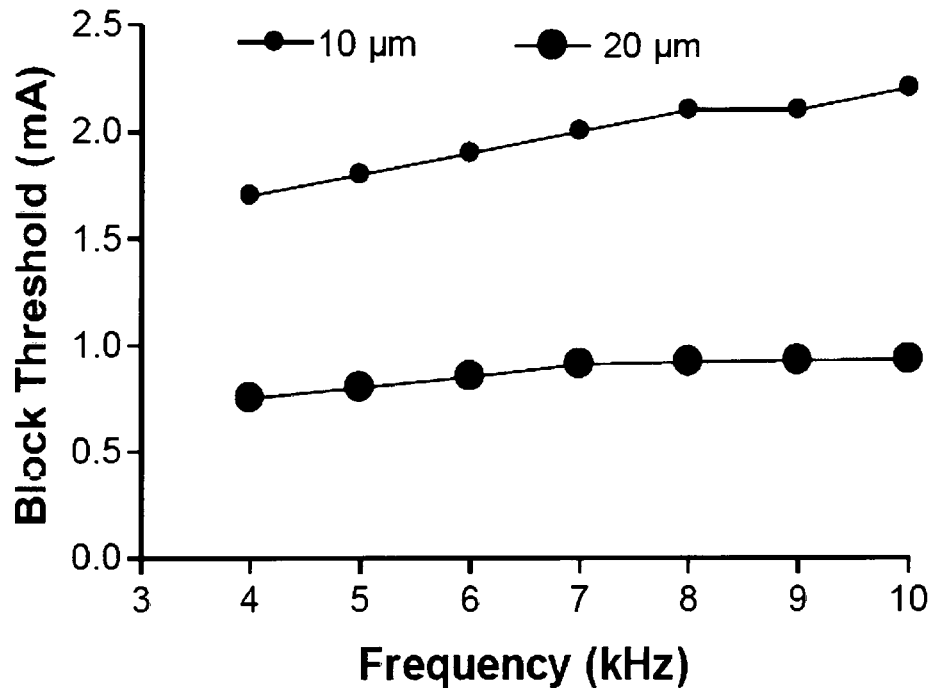
FIG. 9 shows that block threshold is dependent on stimulation frequency and axon diameter.

The model simulation also shows that the block threshold is dependent on HFBS frequency and axon diameter (FIG. 9). A small axon requires a higher intensity to block than a large axon, while a higher frequency also requires a higher intensity to block the axons of same diameter. The frequency dependence was observed in the frog sciatic nerve-muscle preparation (FIG. 3B) where 10 kHz needs higher stimulation intensity than 5 kHz to completely block the nerve conduction. The diameter dependence was also reported in previous animal studies indicating that higher stimulation intensity was required to block small diameter axons. More importantly, this model analysis revealed a minimal blocking frequency of 4 kHz at 20° C. (FIG. 9), which agrees very well with previous animal studies showing a minimal blocking frequency of about 4-5 kHz.

Figure 10:
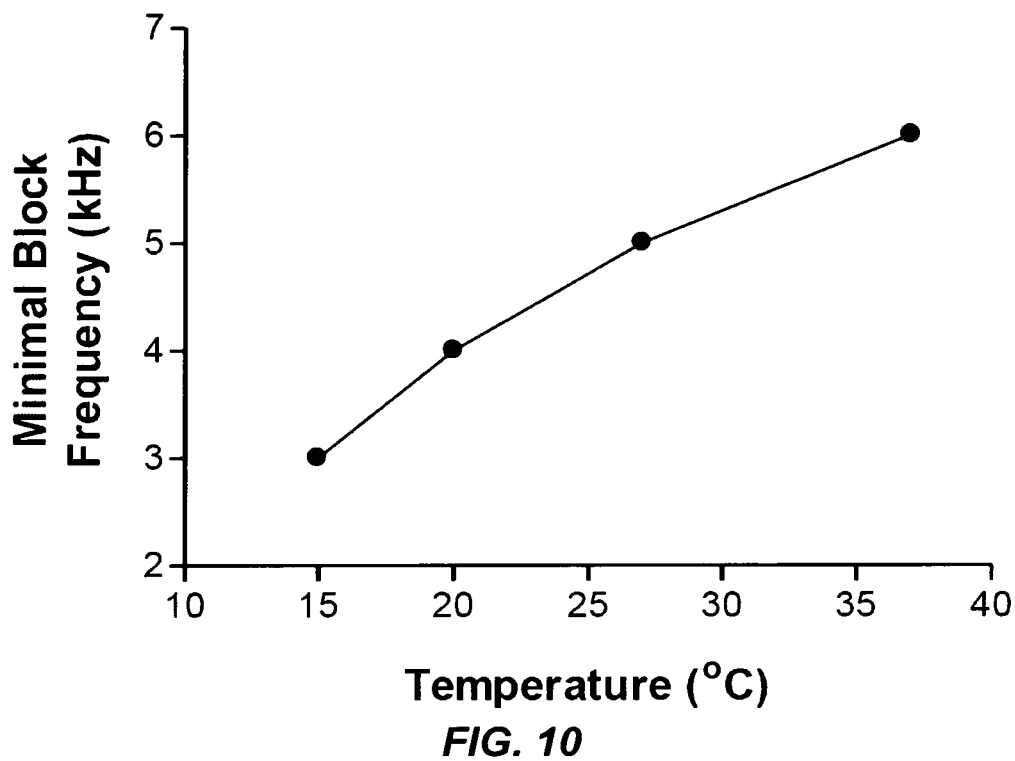
FIG. 10 shows that the minimal stimulation frequency required to block the axonal conduction changes with temperature. Stimulation intensities are at the blocking thresholds. Axon diameter: 10 μm.

This axon model further revealed that the minimal blocking frequency changes with temperature (FIG. 10). At a temperature of 20-27° C., the minimal blocking frequency is about 4-5 kHz. At a lower temperature (15° C.), it could reduce to 3 kHz, while at body temperature (37° C.), it could increase to 6 kHz. A previous study using isolated frog sciatic nerve reported that consistent block could be achieved at a lowest frequency between 3 kHz and 5 kHz at room temperature. It is unfortunate that the specific room temperature was not defined in that study. If it is assumed that the room temperature could vary between 15° C. and 27° C., the minimal blocking frequency of 3-5 kHz obtained in isolated frog sciatic nerve agrees very well with these simulation results as shown in FIG. 10. In addition, a previous study using cats showed that the minimal blocking frequency for HFBS to block the pudendal nerve conduction at body temperature (37° C.) is about 6 kHz, which also agrees very well with the simulation result even though cat pudendal nerve has mammalian myelinated axons while the frog sciatic nerve consists of amphibian myelinated axons.

Figure 11:
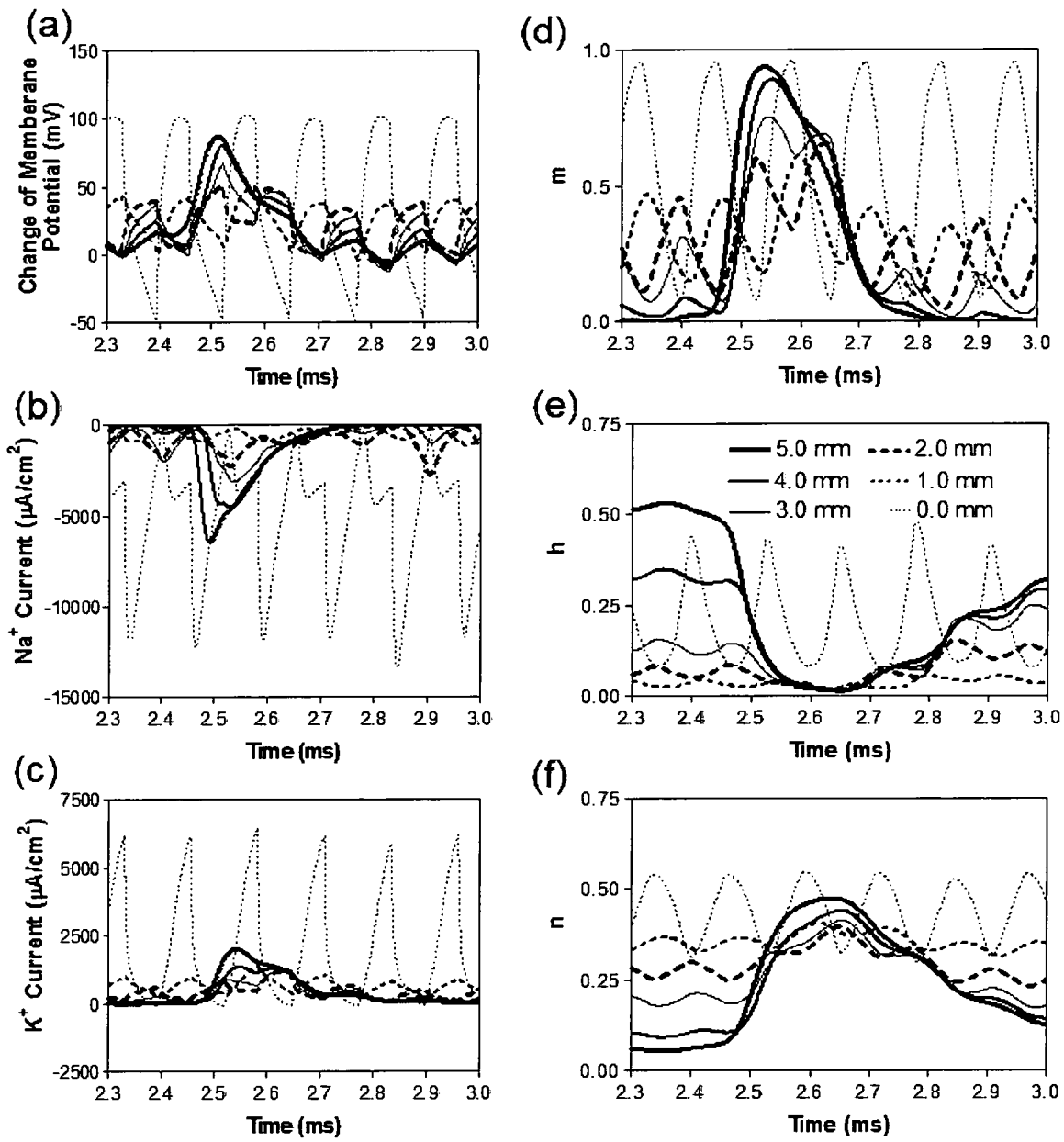
FIG. 11 shows propagation of membrane potentials, ionic currents, and activation/inactivation of the ion channels near the block electrode when nerve conduction block occurs. The legends in (e) indicate the distances of each node to the block electrode (node at 0.0 mm is under the block electrode). m-activation of $Na^+$ channels; h-inactivation of $Na^+$ channels; and n-activation of $K^+$ channels.

In order to understand the possible mechanisms of HFBS block, the changes of membrane potentials, ionic currents, and activation/inactivation of the ion channels near the block electrode when nerve conduction block occurs were investigated. FIG. 11 shows the simulation results using the axon model in FIG. 7. Six consecutive nodes at distances of 0-5 mm from the block electrode are investigated (node at 0.0 mm is under the block electrode). FIG. 11, panels a-c show that the action potential, sodium current, and potassium current are all propagating toward the block electrode, although their amplitudes are gradually attenuating. This propagation is completely abolished at the node (0.0 mm) under the block electrode, where the axon membrane is alternately depolarized and hyperpolarized with large sodium and potassium currents. The behavior of the membrane potentials and ionic currents can be further explained by the activation/inactivation of the sodium and potassium channels as shown in FIG. 11, panels d-f. As the action potential propagates toward the block electrode, the activation (m) of sodium channels also changes at each node and becomes oscillatory at the node under the block electrode (FIG. 11, panel d). Meanwhile, the inactivation (h) of sodium channels is kept at a high level (low value) at nodes of distances 1.0 mm and 2.0 mm to the block electrode (FIG. 11, panel e). Under the block electrode, the inactivation (h) of sodium channels becomes oscillatory. The combination of activation (m) and inactivation (h) of sodium channels (FIG. 11, panels d and e) determines that the amplitude of the sodium current gradually attenuates at nodes close to the block electrode and eventually becomes a pulsed inward current at the node (0.0 mm) under the block electrode (FIG. 11, panel b).

Therefore, the axon model shows that the sodium channels are never completely blocked when conduction block occurs. However, the model does show that the changes in potassium activation (n) induced by the action potentials gradually disappear at the nodes close to the block electrode (FIG. 11, panel f) since the potassium channels become constantly activated at those nodes. The level of potassium channel activation is maximal at the node (0.0 mm) under the block electrode, which results in a large pulsed outward potassium current (FIG. 11, panel c). This large outward potassium current opposes the large inward sodium current, which causes the node (0.0 mm) under the block electrode to become unexcitable leading to block of action potential propagation.

Figure 12:
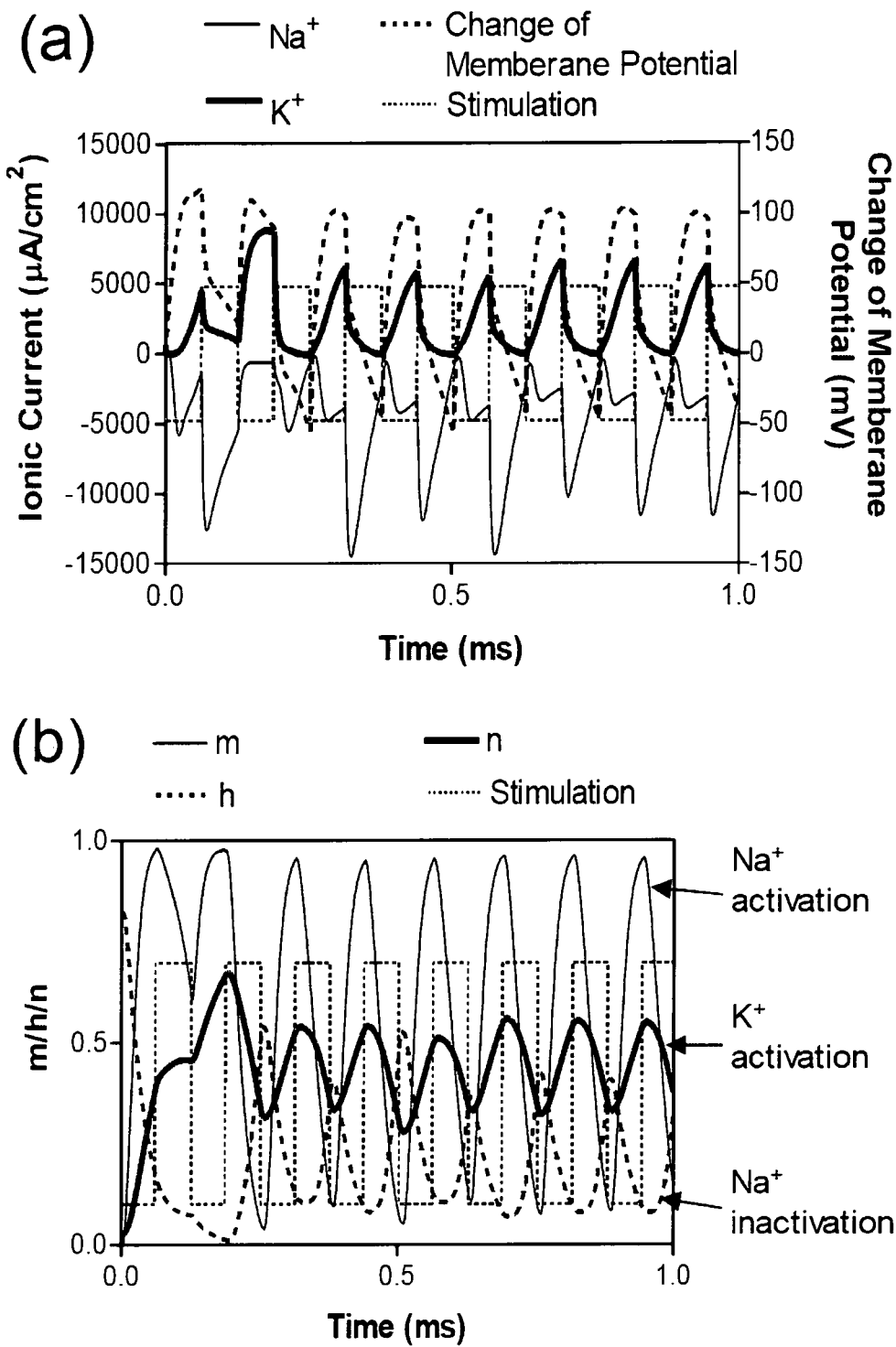
FIG. 12 shows change of membrane potential, ionic currents, and activation/inactivation of the ion channels under the block electrode after the initial action potential induced by high-frequency biphasic stimulation. The stimulation waveform is re-scaled and plotted on the background to show the timing. m activation of $Na^+$ channels; h inactivation of $Na^+$ channels; n activation of $K^+$ channels.

FIG. 12 shows how the node (0.0 mm) under the block electrode is driven by the HFBS into the unexcitable state. The HFBS waveform is also plotted on the background to show the timing. As shown in FIG. 12, panel b, after an initial action potential, the potassium channels are activated (n is around 0.4) resulting in pulsed, outward potassium current (FIG. 12, panel a). Meanwhile, both activation (m) and inactivation (h) of sodium channels becomes oscillatory, which results in pulsed, inward sodium current (FIG. 12, panel a). However, during the depolarization phases (cathodal/negative pulse, see FIG. 12, panel a), the potassium current increases as fast as the sodium current because the potassium channel is already open, which eliminates the delay of potassium current generation relative to the sodium current and thereby causing the node to be unexcitable. The delay between potassium current and sodium current is critical for action potential generation and it can be seen in the first pulse at the beginning of the stimulation (FIG. 12, panel a). This also explains why HFBS cannot generate action potentials after the initial one (see FIG. 8, panel B), even though it alternately depolarizes and hyperpolarizes the membrane (FIG. 12, panel a). Therefore, the axon model reveals that the conduction block induced by HFBS is due to the constant activation of potassium channels under the block electrode.

Figure 13:
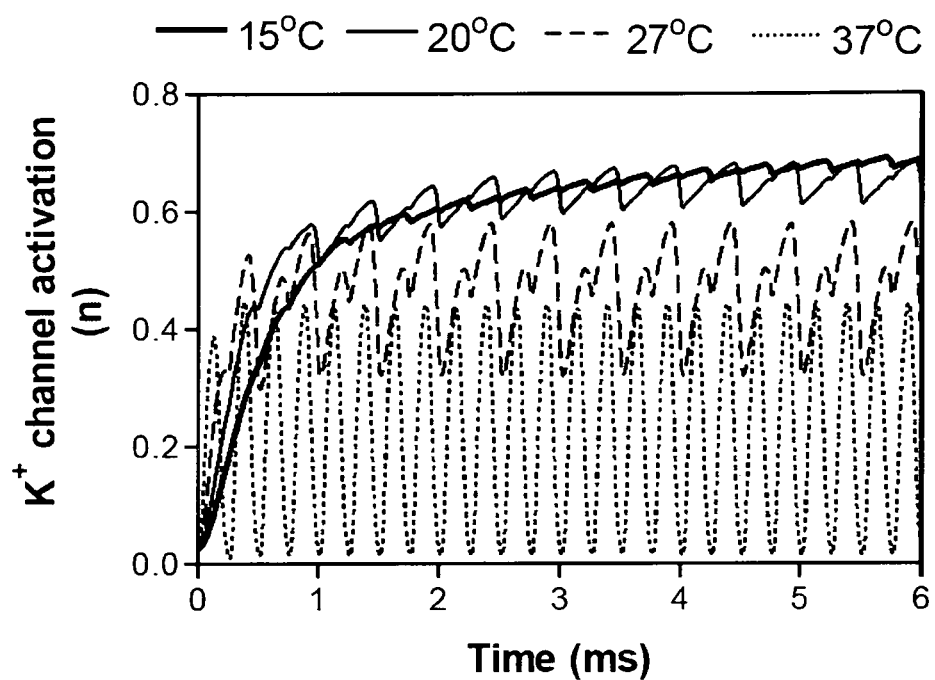
FIG. 13 shows influence of temperature on potassium channel activation (n) in the axonal node under blocking electrode. Stimulation: 4 kHz.

The relationship between temperature and minimal blocking frequency (see FIG. 10) cannot be explained by the hypothesis that HFBS induces a constant depolarization that causes the nerve block. However, it can be explained by the ion channel kinetics. FIG. 13 shows how the activation (n) of potassium channels changes with temperature at a stimulation frequency of 4 kHz. When the temperature changes from 37° C. to 15° C., the potassium channel kinetics become slower. Therefore, the activation (n) of potassium channels changes from oscillation to constant activation at a higher level (around 0.6). At temperatures of 15° C. or 20° C., nerve conduction block can be observed due to the constant activation (n) of potassium channels. This explains why a low frequency (<4 kHz) can only block nerve conduction at a low temperature (e.g., <20° C.) (FIG. 10).

Additionally, if the ionic current $I_{i,n}$ at the nth node (see FIG. 7) is described by Chiu-Ritchie-Rogart-Stagg-Sweeney (CRRSS) model instead of Frankenhaeuser-Huxley model, the minimal blocking frequency at 37° C. increases to 15 kHz. This is because the CRRSS model is derived from rabbit myelinated nerves that lack the potassium current in the membrane kinetics. Without potassium channels in the model, a greater than 15 kHz frequency is required, which is consistent with the faster sodium channel kinetics and the need for a higher frequency to drive the sodium channel into inactivation to induce a nerve conduction block. The results from the CRRSS model further indicate that it is the potassium channel kinetics that determine the minimal blocking frequency to be 4-5 kHz.

These simulation studies not only reveal the mechanism underlying acute nerve block that can be produced by HFBS within seconds after starting the stimulation (see FIGS. 4, 11, and 12), they also have significant implications to the mechanisms underlying post-stimulation block observed in the animal study (FIGS. 5 and 6). Since HFBS generates outward potassium current and inward sodium current during each biphasic stimulation pulse (FIG. 12), a prolonged HFBS will certainly produce an accumulative effect to change the intracellular and extracellular ion concentrations. Therefore, at some time point during a prolonged HFBS the accumulative effects on intracellular and extracellular ion concentrations will be large enough to cause axonal conduction block. This axonal conduction block will be maintained after terminating the prolonged HFBS, producing a post-stimulation block (see FIGS. 5 and 6) because the ion pump will need time to slowly recover the ion concentrations changed by prolonged HFBS. More importantly, HFBS is not required to have a super-threshold intensity to produce the post-stimulation block because sub-threshold HFBS can also generate the pulsed sodium and potassium current (FIG. 12) but will require a longer time than super-threshold HFBS to accumulate enough change in the ion concentrations to produce axonal conduction block. The results presented herein reveal that the mechanisms underlying acute and post-stimulation block are different.

Example 3 Pudendal Nerve Block by a Sub-Threshold High-Frequency (kHz) Biphasic Stimulation The objective of this example was to show that the excitation threshold of high-frequency (10 kHz) biphasic stimulation (HFBS) can be increase with time in pudendal nerve of a cat.

Experimental Preparation

A single cat was anesthetized by isoflurane (2-5% oxygen) during surgery and switched to α-chloralose anesthesia (initial 65 mg/kg i.v. with supplemental as needed) during data collection. The right cephalic vein was catheterized for administration of fluid or anesthetics. The airway was kept patent by a tracheotomy. A catheter was inserted into the right carotid artery to monitor the blood pressure. A pulse oximeter (9847V; NONIN Medical, Plymouth, MN) was attached to the tongue to monitor the heart rate and blood oxygen.

Figure 14:
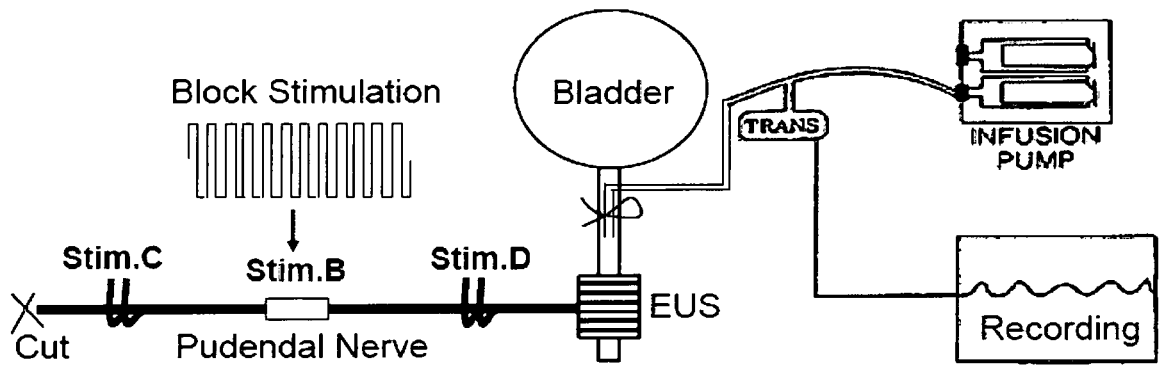
FIG. 14 shows an experimental setup for applying sub-threshold blocking stimulation to the pudendal nerve. Blocking stimulation is applied to the pudendal nerve with a tripolar cuff electrode (Stim.B) to block propagation of the action potential induced by bipolar hook electrode at a central site (Stim.C). Another bipolar hook electrode is placed at a distal site (Stim.D) to confirm that the external urethral sphincter (EUS) is blocked and not merely fatigued. The urethra is slowly perfused by an infusion pump so that the EUS contraction can be recorded by the increase in urethral pressure.

Via an abdominal incision, a catheter was inserted into the distal urethra to slowly (1 ml/min) perfuse the urethra with saline and record urethral pressure increase caused by contractions of external urethral sphincter (EUS) that was induced by pudendal nerve stimulation (FIG. 14). The ureters were tied, cut, and drained externally. The left pudendal nerve was exposed via a 3-4 cm incision in the sciatic notch lateral to the tail for implantation of a tripolar cuff electrode (NEC113, MicroProbes Inc, Gaithersburg, MD, USA) to deliver HFBS (Stim.B in FIG. 14). Two hook electrodes were placed central (Stim.C) and distal (Stim.D) to the tripolar cuff electrode. The right pudendal nerve was also exposed and implanted with the same 3 sets of electrodes. Pudendal nerves were transected centrally to prevent reflex activation of the EUS (FIG. 14). Stimulation pulses (20 Hz, 0.2 ms) generated by a stimulator (Grass S88, Grass Technologies, RI, USA) were delivered via a stimulation isolator (SIU5, Grass Technologies, RI, USA) to the hook electrodes (Stim.C or Stim.D) to induce >30 cmH$_2$O urethral pressure. HFBS (6 or 10 kHz square waveform without a pulse interval, see FIG. 14) generated by a computer running a LabView program (National Instrument, TX, USA) was delivered via a stimulation isolator (A395, World Precision Instruments, FL, USA) to the tripolar cuff electrode to block pudendal nerve conduction and suppress EUS contractions induced by Stim.C (FIG. 14).

Results

Figure 15:
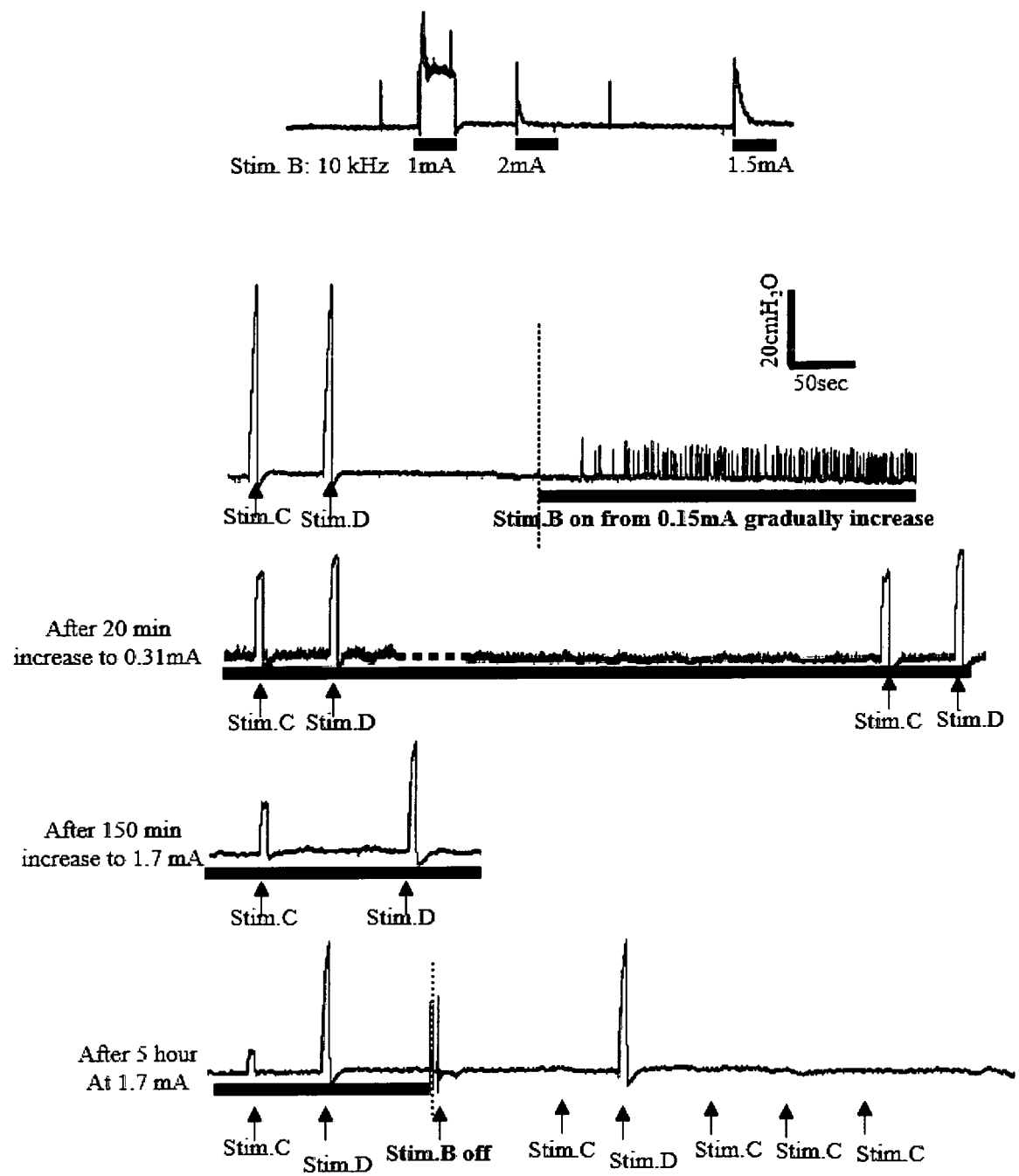
FIG. 15 shows that the threshold for exciting a nerve can be increased through gradually increasing the stimulation intensity from a very low intensity to change the ionic concentration, resulting in a block of nerve conduction.

FIG. 15 shows that Stim.C and Stim.D induced the same EUS contractions before the 10 kHz HFBS was applied at Stim.B. Stim.B was then applied for more than 5 hours starting at a sub-threshold intensity of 0.15 mA. When the 0.15 mA sub-threshold intensity was gradually increased to 0.16-0.2 mA during the first several minutes of stimulation, it induced irregular weak EUS twitches that were disappeared as the HFBS gradually increased the excitation threshold during a period of 20 minute stimulation. Then, further slowly increasing the HFBS intensity to 1.7 mA during a period of 150 minutes did not induce any EUS contraction, but it greatly blocked the EUS contraction induced by Stim.C (but not by Stim.D), indicating a conduction block of the pudendal nerve locally at the site of Stim.B. Maintaining the HFBS at 1.7 mA for 5 hours further changed the intracellular/extracellular ion concentrations, which resulted in further pudendal nerve block and thereby the further reduction in EUS contraction induced by Stim.C, while the EUS contractions induced by Stim.D was still strong (indicating that the nerve was blocked, and that it was not merely muscle fatigue that contributed to the notable change in induced contractions). After termination of the HFBS, the pudendal nerve block was maintained in hours.

The result in FIG. 15 clearly indicates that sub-threshold HFBS can gradually increase nerve excitation threshold with time and the intensity of HFBS can be gradually increased while always maintaining below the increased excitation threshold. Eventually, the HFBS intensity can be increased high enough to block pudendal nerve conduction and this block is persistent for many hours after termination of the HFBS, i.e., a post-HFBS block.

DISCUSSION

This study in cats confirmed that post-HFBS block can occur locally on the pudendal nerve instead of fatiguing the muscle (FIG. 15).

Our previous computer simulation studies employing unmyelinated (Hodgkin-Huxley model) and myelinated (Frankenhaeuser-Huxley model) axonal models have shown that each pulse of the HFBS can induce an inward sodium current and an outward potassium current, which will certainly increase the concentrations of intracellular sodium and extracellular potassium ions. The HFBS used in this study has a continuous waveform without an interval between the square pulses (FIG. 14), which leaves no time for the sodium-potassium pump to recover the ion concentrations. Therefore, if HFBS continues for a long time, it will accumulatively increase the intracellular sodium and extracellular potassium concentrations to the levels that are high enough to block axonal conduction. This block will be maintained after termination of the HFBS until the sodium-potassium pump can restore the normal ion concentrations. Hence, the recovery period for post-HFBS block should depend on: 1. the speed of the sodium-potassium pump; and/or 2. the total increases in ion concentrations.

As also shown in FIG. 15, the initial nerve firing induced by 10 kHz HFBS can be prevented as the HFBS continues. Since the HFBS will gradually change the ion concentrations, the excitation threshold will increase with time. Therefore, the intensity of sub-threshold HFBS can be increased to a new sub-threshold level after minutes or hours of stimulation. Similarly, the new sub-threshold will be further increased with stimulation time and the intensity of the HFBS can be repeatedly increased while always being kept at a sub-threshold level without exciting the nerve. Eventually, HFBS can reach an intensity high enough to produce large changes in ion concentrations causing a nerve conduction block.

This study using cat pudendal nerve provides scientific evidence supporting the hypothesis that post-HFBS block is due to the changes in intracellular/extracellular ion concentrations produced by prolonged HFBS. Understanding the mechanisms of HFBS block is important to develop new methods to block nerve conduction or improve current clinical applications of HFBS to treat chronic disorders.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments.

What is claimed is:

1. A method of blocking a nerve or neuron, comprising: applying an electrical stimulation to the nerve or neuron, wherein the electrical stimulation comprises charge-balanced, biphasic, symmetric electrical pulses and is of an intensity that does not cause nerve or neuron excitation, for a length of time sufficient to produce a block of nerve conduction or neuron excitation.

2. The method of claim 1, wherein the intensity of the electrical stimulation is below an initial excitation threshold of the nerve or neuron.

3. The method of claim 2, wherein the stimulation is applied at an intensity below the initial excitation threshold of the nerve or neuron for a length of time sufficient to cause an increase of the initial excitation threshold of the nerve or neuron to a first increased excitation threshold.

4. The method of claim 3, further comprising increasing the intensity of the electrical stimulation to a first increased intensity electrical stimulation above the initial excitation threshold of the nerve or neuron and below the first increased excitation threshold of the nerve or neuron for a length of time sufficient to cause an increase of the first increased excitation threshold of the nerve or neuron to a second increased excitation threshold.

5. The method of claim 4, further comprising increasing the intensity of the first increased intensity electrical stimulation to a second increased intensity electrical stimulation above the first increased excitation threshold of the nerve or neuron and below the second increased excitation threshold of the nerve or neuron for a length of time sufficient to cause an increase of the second excitation threshold of the nerve or neuron to a third increased excitation threshold.

6. The method of claim 4, wherein the first increased intensity electrical stimulation, the second increased intensity electrical stimulation, and/or any additional increased intensity electrical stimulation are delivered for a period of from 100 milliseconds to 14 days.

7. The method of claim 3, wherein, as a result of increasing the initial excitation threshold to the first or second or third or any additional increased excitation threshold, the nerve is blocked from conducting action potentials or the neuron is blocked from generating action potentials.

8. The method of claim 1, wherein the electrical stimulation is delivered at an intensity of 0.01 mA to 10 mA and/or 1 mV to 10,000 mV.

9. The method of claim 1, wherein the electrical stimulation is delivered at a frequency of 1 Hz to 50 kHz.

10. The method of claim 1, wherein the electrical stimulation is delivered for a period of from 1 minute to 14 days.

11. The method of claim 1, further comprising, once block of nerve conduction or neuron excitation is achieved, stopping application of the electrical stimulation for a period of at least 1 minute, wherein the block of nerve conduction or neuron excitation is maintained during the period and, after the period has concluded, resuming electrical stimulation of the nerve or neuron at the same or a lower intensity to continue or prolong the block of nerve conduction or neuron excitation.

12. The method of claim 1, further comprising, once block of nerve conduction or neuron excitation is achieved, maintaining the block by reducing the intensity of the electrical stimulation or increasing the frequency of the electrical stimulation.

13. A device comprising:
a controller;
a pulse generator in communication with the controller; and
one or more skin surface electrodes or magnetic coils in electrical communication with the pulse generator, wherein
the controller is programmed or configured to cause the pulse generator, through the one or more skin surface electrodes or magnetic coils, to apply an electrical stimulation to a nerve or neuron, wherein the electrical stimulation comprises charge-balanced, biphasic, symmetric electrical pulses and is of an intensity below an initial excitation threshold of the nerve or neuron, for a length of time sufficient to produce a block of nerve conduction or neuron excitation.

14. The device of claim 13, wherein the controller is programmed or configured to cause the pulse generator, through the one or more skin surface electrodes or magnetic coils, to deliver electrical stimulation through the one or more skin surface electrodes or magnetic coils at an intensity of 0.01 mA to 10 mA and/or 1 mV to 10,000 mV.

15. The device of 29, wherein the controller is programmed or configured to cause the pulse generator, through the one or more skin surface electrodes or magnetic coils, to deliver electrical stimulation through the one or more skin surface electrodes or magnetic coils at a frequency of 1 Hz to 50 kHz, for from 100 milliseconds to 14 days, wherein the electrical stimulation comprises biphasic, charge-balanced electrical pulses.

16. The device of claim 13, wherein the controller is further programmed or configured to cause the pulse generator, through the one or more skin surface electrodes or magnetic coils, to apply electrical stimulation at an intensity below the initial excitation threshold of the nerve or neuron for a length of time sufficient to cause an increase of the initial excitation threshold of the nerve or neuron to a first increased excitation threshold.

17. The device of claim 16, wherein the controller is further programmed or configured to cause the pulse generator to increase the intensity of the electrical stimulation to a first increased intensity electrical stimulation above the initial excitation threshold of the nerve or neuron and below the first increased excitation threshold of the nerve or neuron for a length of time sufficient to cause an increase of the first increased excitation threshold of the nerve or neuron to a second increased excitation threshold.

18. The device of claim 17, wherein the controller is further programmed or configured to cause the pulse generator to increase the intensity of the first increased intensity electrical stimulation to a second increased intensity electrical stimulation above the first increased excitation threshold of the nerve or neuron and below the second increased excitation threshold of the nerve or neuron for a length of time sufficient to cause an increase of the second excitation threshold of the nerve or neuron to a third increased excitation threshold.

19. A method of blocking a nerve or neuron, comprising:
applying an electrical stimulation to the nerve or neuron at a frequency of about 1 kHz to about 4 kHz, wherein the electrical stimulation comprises charge-balanced, biphasic, symmetric electrical pulses and is of an intensity that does not cause nerve or neuron excitation, for a length of time sufficient to produce a block of nerve conduction or neuron excitation.

* * * * *

UNITED STATES PATENT AND TRADEMARK OFFICE
CERTIFICATE OF CORRECTION

PATENT NO. : 11,865,346 B2
APPLICATION NO. : 17/047754
DATED : January 9, 2024
INVENTOR(S) : Changfeng Tai It is certified that error appears in the above-identified patent and that said Letters Patent is hereby corrected as shown below:

In the Claims

Column 29, Line 23, Claim 15, after "of" insert -- claim --

Column 29, Line 23, Claim 15, delete "29," and insert -- 13, --

Signed and Sealed this
Nineteenth Day of March, 2024

Katherine Kelly Vidal
*Director of the United States Patent and Trademark Office*